United States Patent
Bhatnagar et al.

(10) Patent No.: US 6,770,079 B2
(45) Date of Patent: *Aug. 3, 2004

(54) APPARATUS AND METHOD FOR FIXATION OF OSTEOPOROTIC BONE

(75) Inventors: Mohit Bhatnagar, Gaithersburg, MD (US); Eric Major, Ashburn, VA (US)

(73) Assignee: American Osteomedix, Inc., Leesburg, VA (US)

( * ) Notice: Subject to any disclaimer, the term of this patent is extended or adjusted under 35 U.S.C. 154(b) by 39 days.

This patent is subject to a terminal disclaimer.

(21) Appl. No.: 09/983,740

(22) Filed: Oct. 25, 2001

(65) Prior Publication Data

US 2002/0049449 A1 Apr. 25, 2002

Related U.S. Application Data

(63) Continuation-in-part of application No. 09/525,008, filed on Mar. 14, 2000.
(60) Provisional application No. 60/270,867, filed on Feb. 26, 2001, provisional application No. 60/242,707, filed on Oct. 25, 2000, provisional application No. 60/167,017, filed on Nov. 23, 1999, provisional application No. 60/133,276, filed on May 10, 1999, and provisional application No. 60/124,661, filed on Mar. 16, 1999.

(51) Int. Cl.[7] .............................................. A61B 17/58
(52) U.S. Cl. .................................... 606/94; 606/86
(58) Field of Search .................................. 606/92–94

(56) References Cited

U.S. PATENT DOCUMENTS

| | | | | |
|---|---|---|---|---|
| 3,223,083 A | | 12/1965 | Cobey | |
| 4,793,363 A | * | 12/1988 | Ausherman et al. | 600/567 |
| 4,922,602 A | | 5/1990 | Mehl | |
| 5,108,404 A | | 4/1992 | Scholten et al. | |
| 5,312,375 A | | 5/1994 | Gurmarnik | |
| 5,389,070 A | | 2/1995 | Morell | |
| 5,693,021 A | * | 12/1997 | Diaz et al. | 604/187 |
| 5,718,707 A | | 2/1998 | Mikhail | |
| 5,741,261 A | | 4/1998 | Moskovitz et al. | |
| 5,824,087 A | | 10/1998 | Aspden et al. | |
| 5,925,051 A | | 7/1999 | Mikhail | |
| 5,989,260 A | * | 11/1999 | Yao | 606/102 |
| 6,019,776 A | | 2/2000 | Preissman et al. | |
| 6,113,576 A | * | 9/2000 | Dance et al. | 604/164.01 |
| 6,241,734 B1 | | 6/2001 | Scribner et al. | |
| 2002/0019664 A1 | * | 2/2002 | Douglas | 623/1.35 |
| 2002/0043542 A1 | * | 4/2002 | Chan | 222/386 |

FOREIGN PATENT DOCUMENTS

WO        WO 90/04364        5/1990

* cited by examiner

Primary Examiner—Cary E. O'Connor
Assistant Examiner—Candice C. Melson
(74) Attorney, Agent, or Firm—Piper Rudnick LLP; Perry E. Van Over

(57) ABSTRACT

A Novel surgical apparatus and method of use in osteoplasty and other methods of injecting materials into a subject for medical purposes. The present invention particularly relates to the surgical treatment of traumatic, pathogenic, or osteoporotic bone conditions of the human and other animal body systems and more particularly, to a novel apparatus and method for injection of a material into a lesion of a vertebral body or other bony structure.

32 Claims, 23 Drawing Sheets

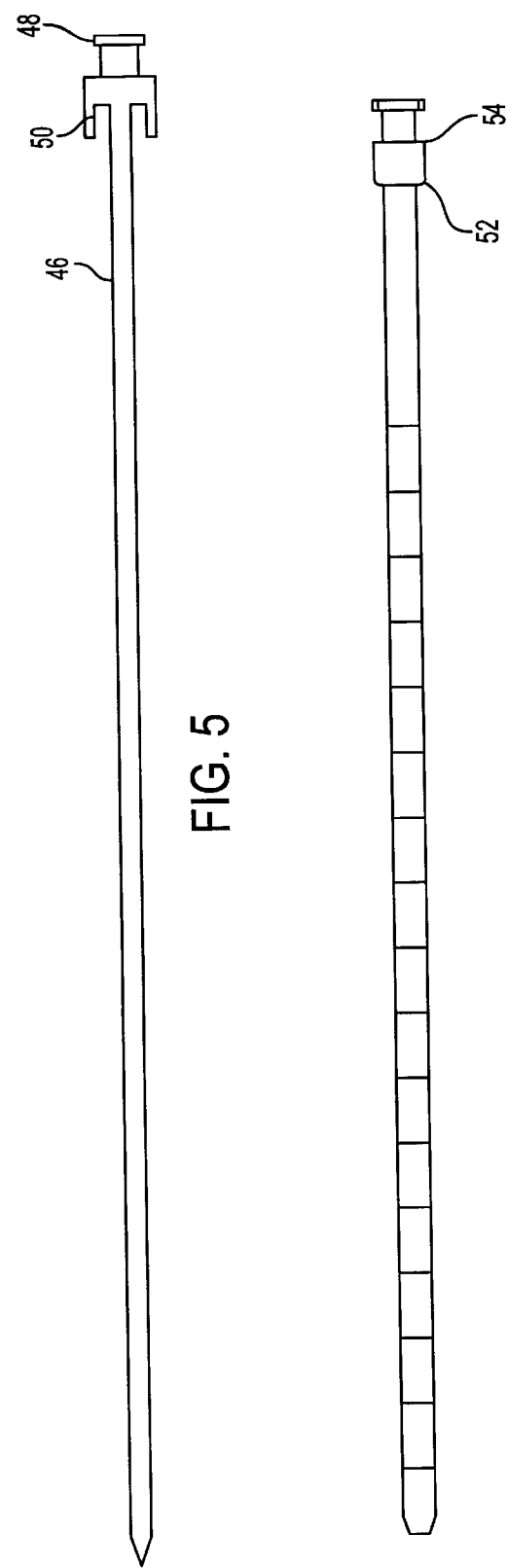

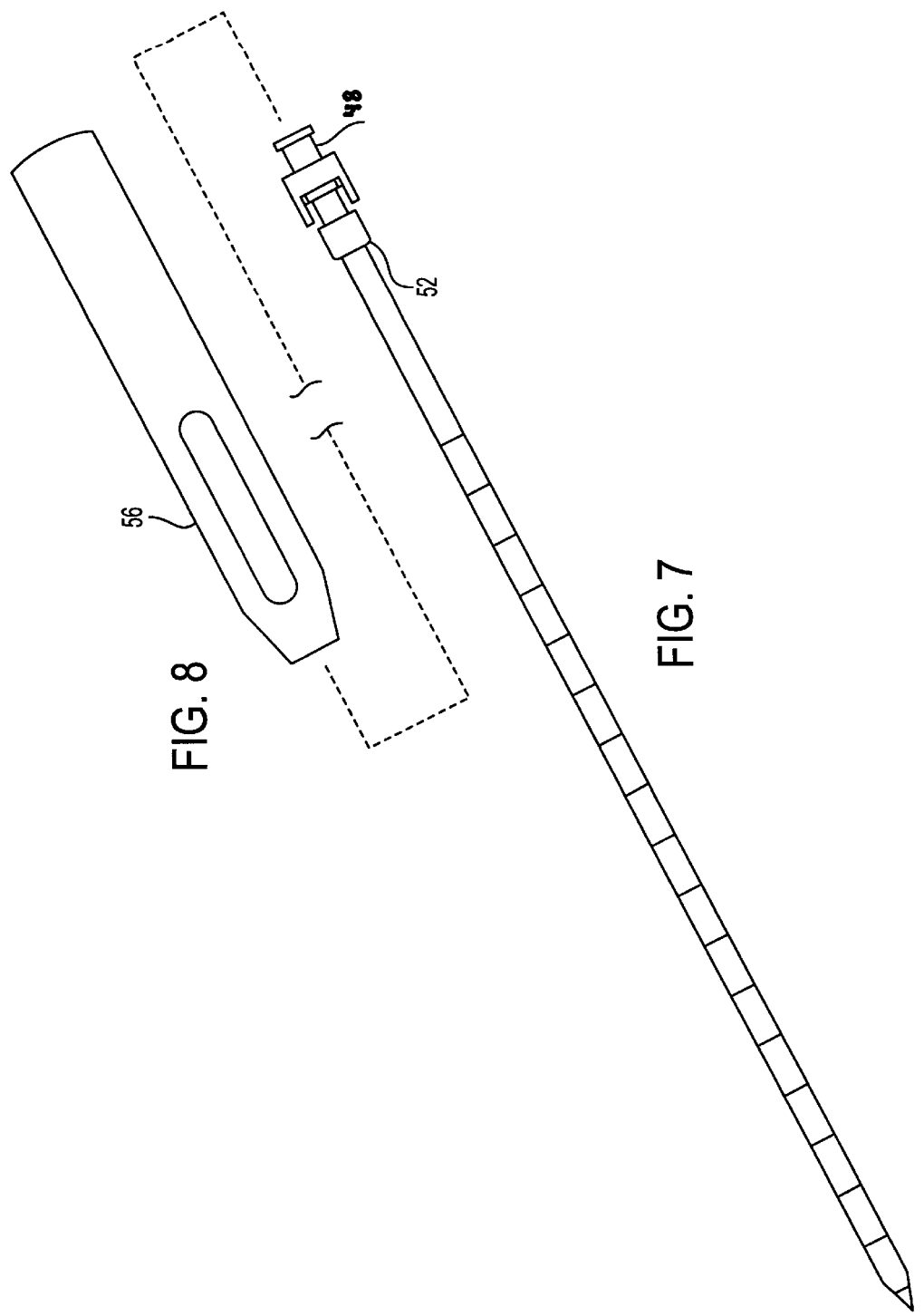

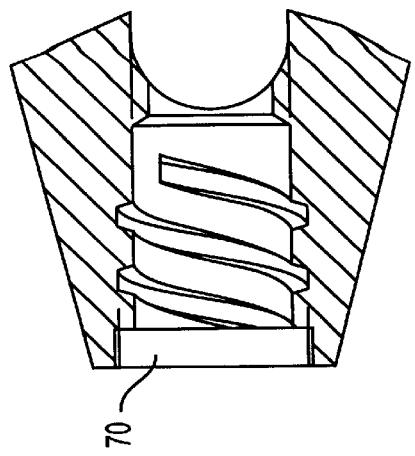
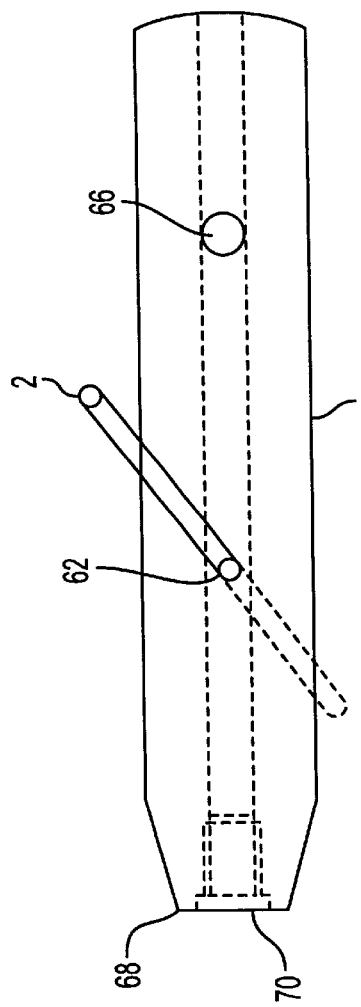
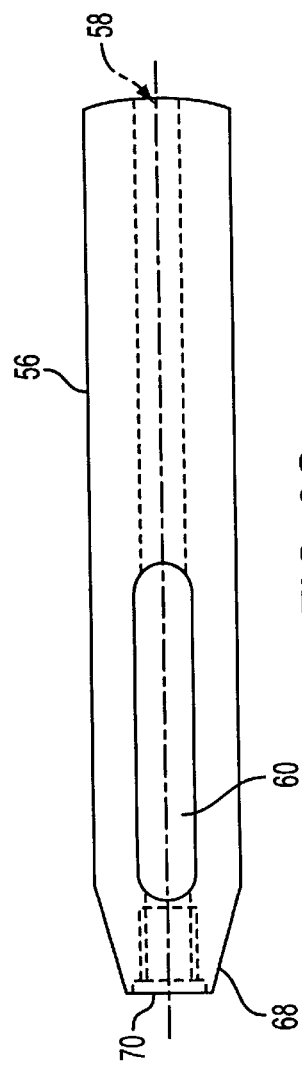
FIG. 9B
FIG. 9A
FIG. 9C

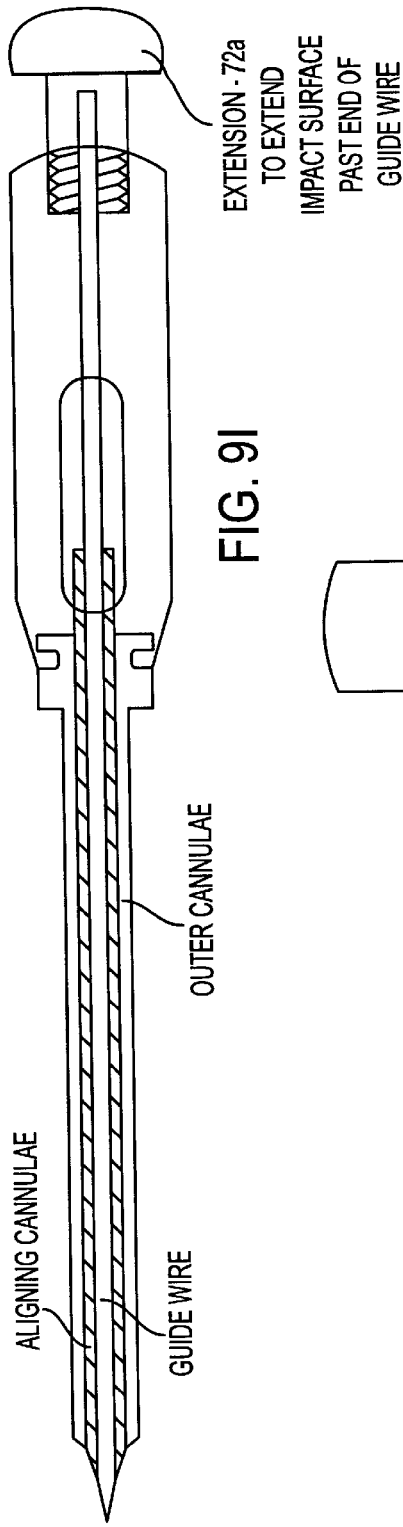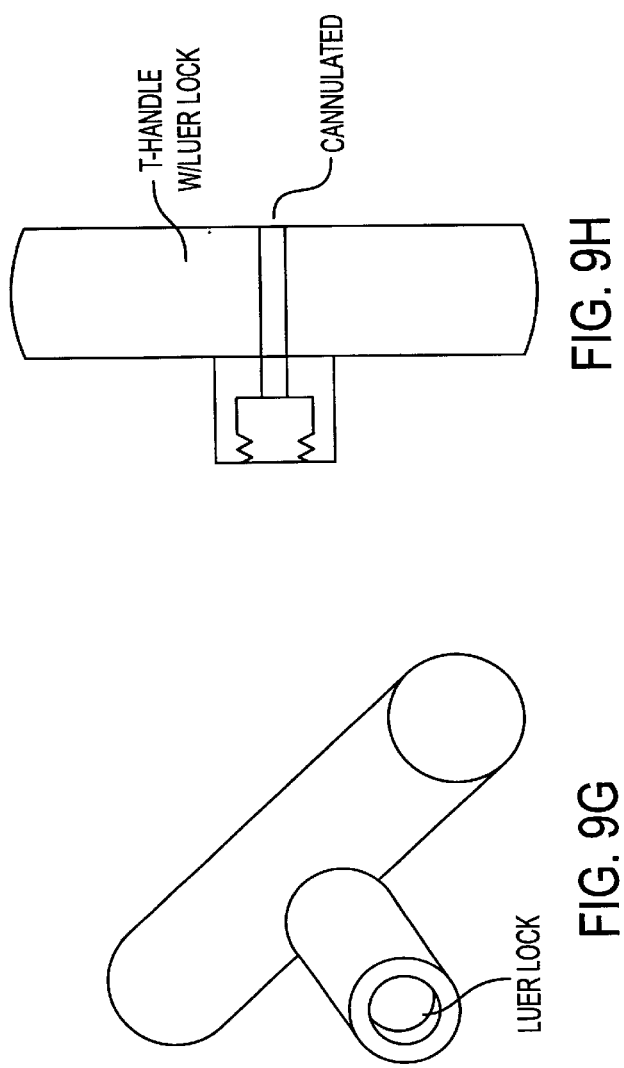

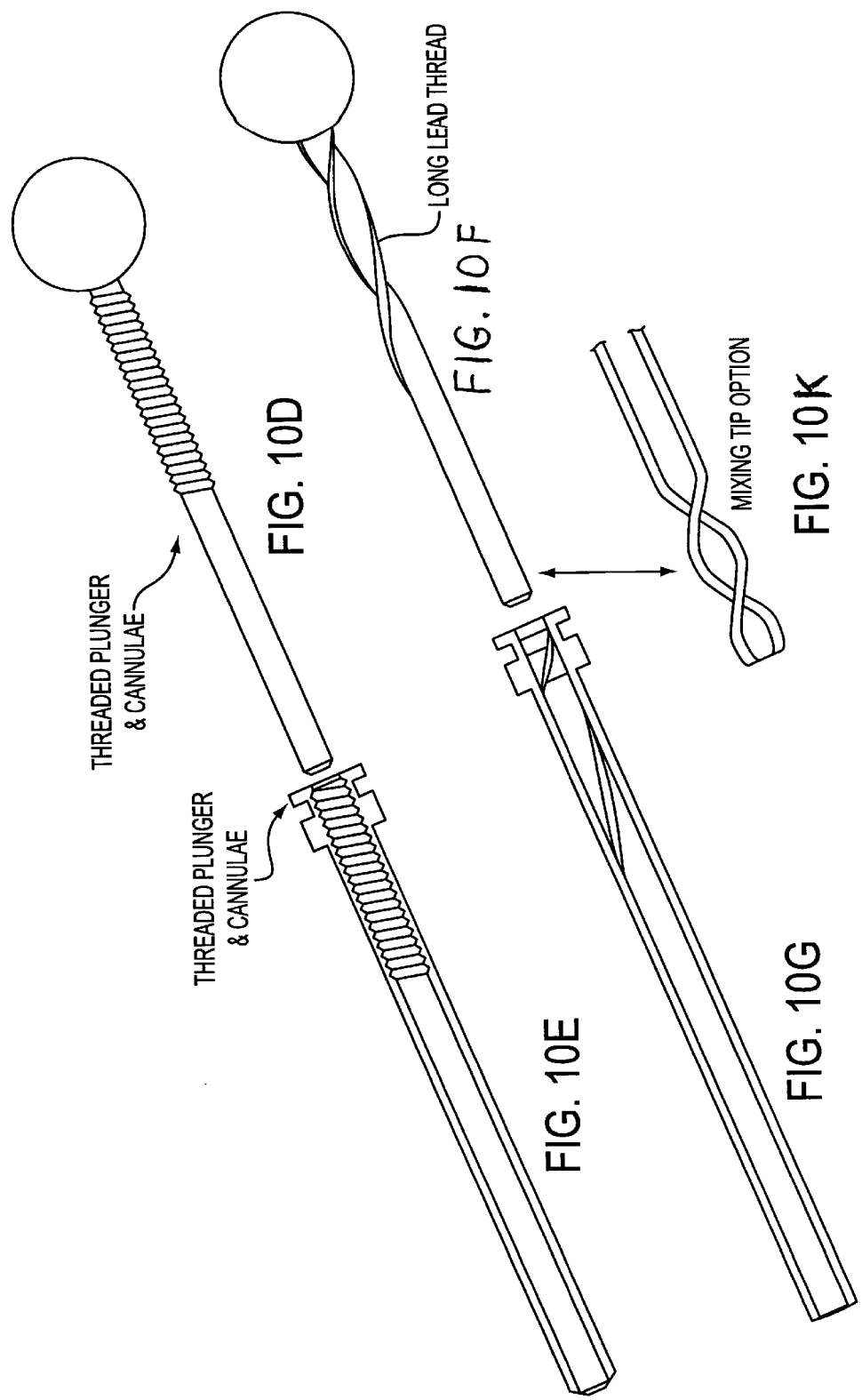

SWIVEL BALL ON PLUNGER

SWIVEL BALL ON PLUNGER
82a

LUER LOCK PLUNGER BALL

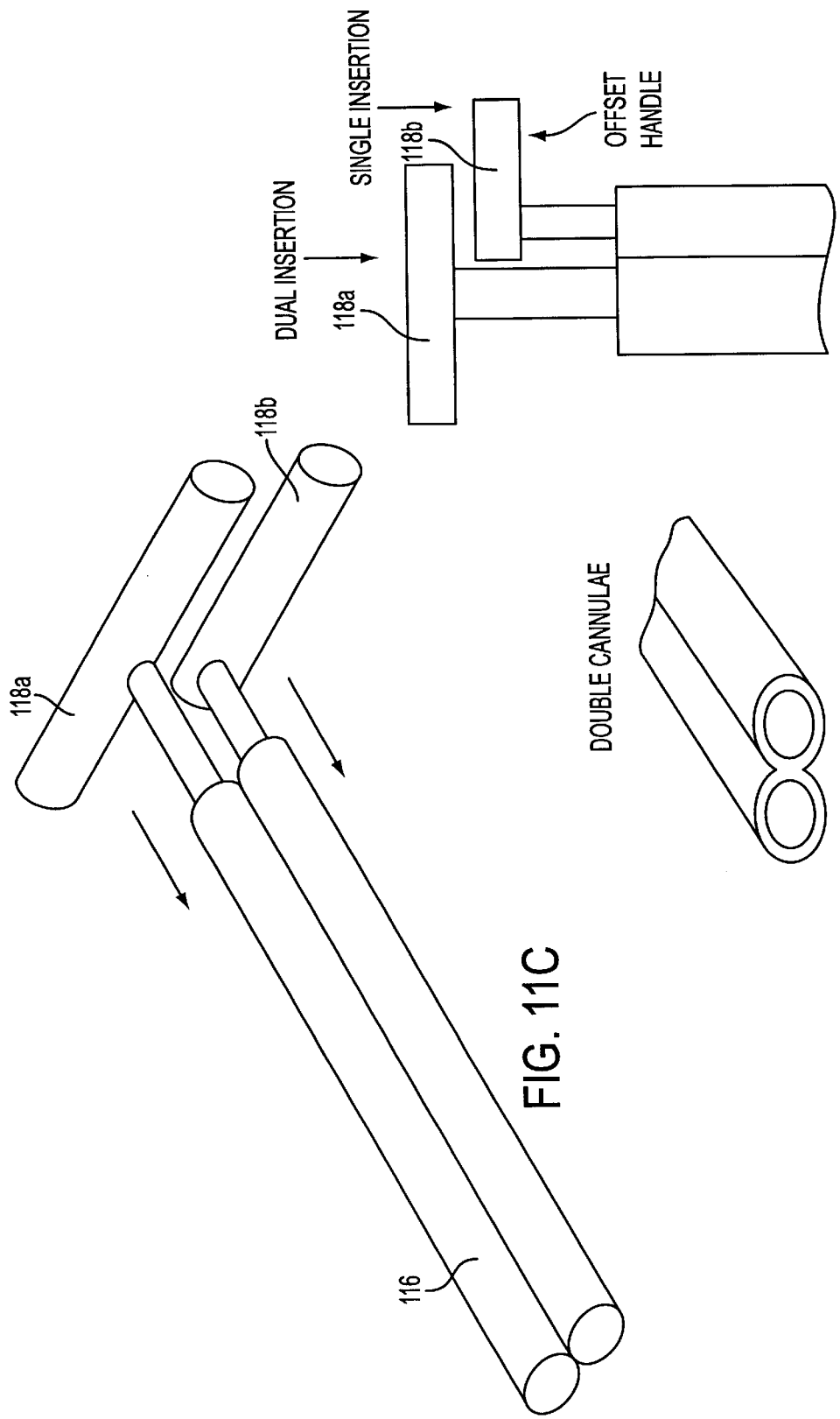

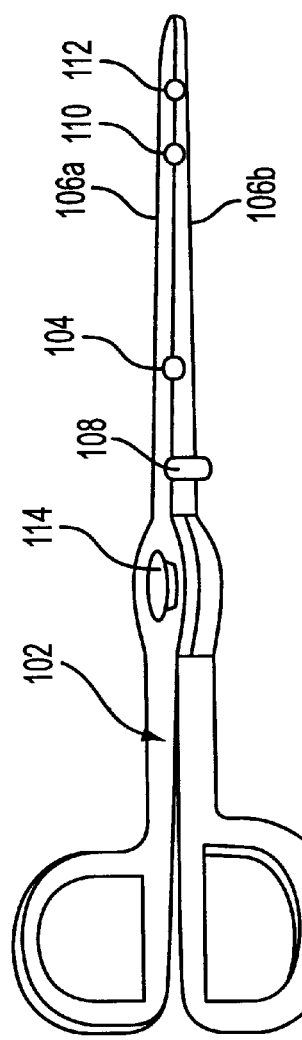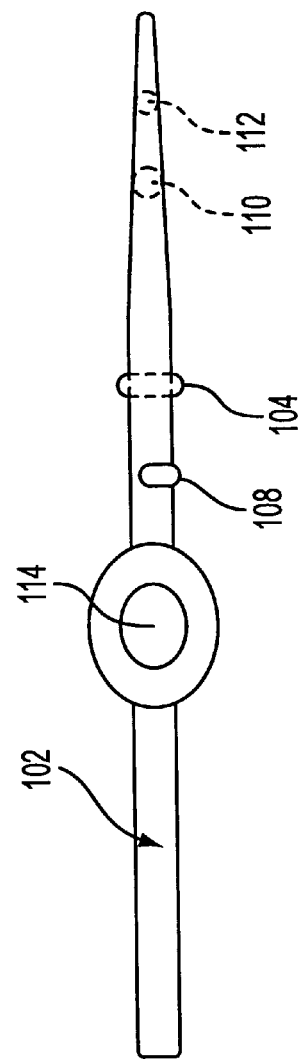
FIG. 13A
FIG. 13B

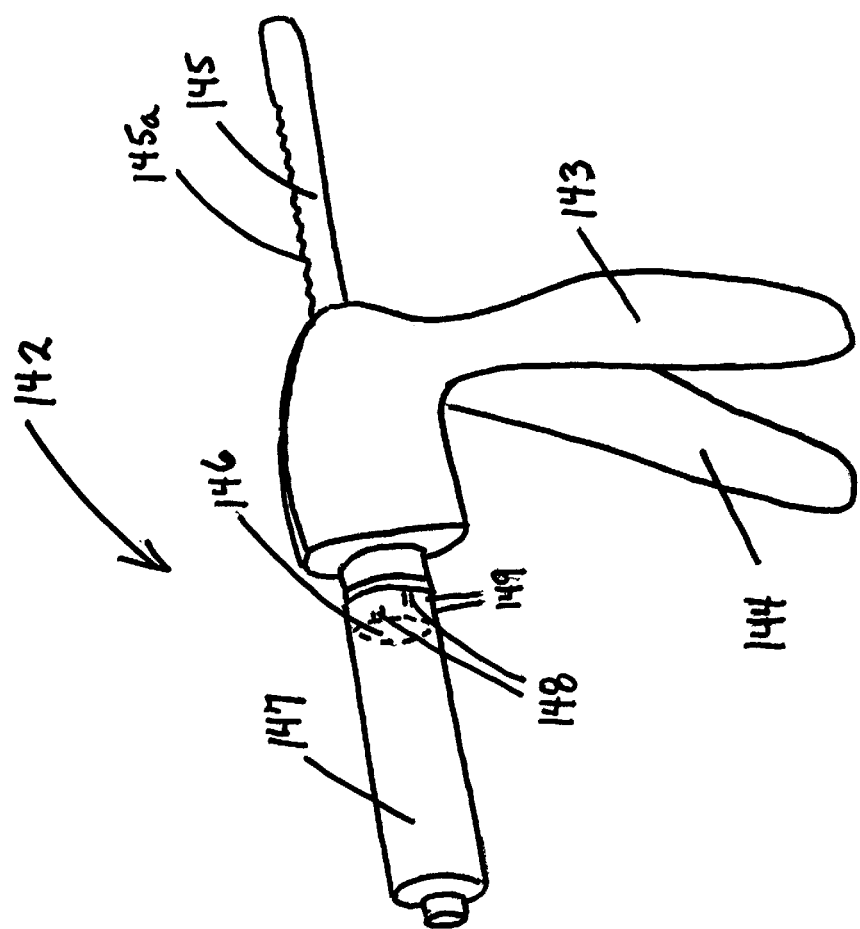

APPARATUS AND METHOD FOR FIXATION OF OSTEOPOROTIC BONE

This application is a Continuation-In-Part of U.S. patent application Ser. No. 09/525,008, filed Mar. 14, 2000, which claimed priority to U.S. Provisional Patent Application No. 60/124,661 filed Mar. 16, 1999, U.S. Provisional Patent Application No. 60/133,276 filed May 10, 1999, and U.S. Provisional Patent Application No. 60/167,017 filed Nov. 23, 1999. U.S. patent application Ser. No. 09/525,008 was also filed as PCT Application No. PCT/US00/06643 on Mar. 15, 2000. The present Continuation-In-Part application also claims priority to U.S. Provisional Patent Application No. 60/242,707 filed Oct. 25, 2000 and U.S. Provisional Application No. 60/270,867 filed Feb. 26, 2001.

This invention relates to a novel surgical apparatus for use in osteoplasty and other methods of injecting materials into a subject for medical purposes. Particularly, the present invention relates to the surgical treatment of traumatic, pathogenic, or osteoporotic bone conditions of the human and other animal body systems and more particularly, to a novel apparatus and method for injection of a material into a lesion of a vertebral body or other bony structure.

BACKGROUND

Lesions within the bone can result from osteoporosis, tumor, or other pathogenic causes. Most common among the elderly population is the degenerative effect of osteoporosis, particularly the female elderly. Osteoporosis is mediated at least in part by genetic defects and a fall in circulating estrogen levels. Although calcium replacement therapy can have some beneficial effects, the larger doses of calcium involved have other less helpful consequences and accordingly, the prognosis for those with bone demineralization is not particularly good. Of great concern is the fact that every year in the United States there occurs approximately 1.2 million bone failures due to osteoporosis. Vertebral compression failures are a major orthopedic health concern of the elderly due to the long term debilitating nature of the injury.

Historically, osteoporotic vertebral body compression failures have been treated with bed rest, analgesics, and intravenous hydration during the first week after onset of the problem. These steps are followed by the prescription of a soft or firm spinal corset, depending upon the physician's preference. In most cases the corset is not worn because the patient suffers much discomfort and oftentimes greater discomfort than that due to the failure of the vertebral body. In any case, this conventional approach required extensive hospitalization and bed rest, which often results in very limited success, chronic pain, and further osteoporosis with worsening conditions of the vertebral body. The costs associated with such extended hospitalization and the negative effect on the general health of the patient from such prolonged inactivity should be avoided if possible.

Traditional surgical techniques employed to alleviate vertebral compression failures can involve major invasive surgical techniques with all of the possible negative consequences. Such techniques have typically required prolonged patient recuperation and unfortunately have met with limited success in alleviating pain and returning the patient to a normal life style.

More recently efforts have been made to develop surgical techniques for repair of vertebral compression failures of osteoporotic bone by using conventional instruments in a transpedicular approach to penetrate the vertebral body, including a standard syringe, and then inject a flowable synthetic bone material or bone cement directly into the vertebral body through the syringe. This technique of vertebroplasty requires that the physician take the utmost care to avoid damage to the spinal cord when drilling through the narrow dimensions of the pedicle of the vertebrae. To avoid potentially catastrophic results physicians practicing conventional vertebroplasty require the use of CAT scanning, biplane fluoroscopy, magnetic resonance imaging, or other imaging devices to ensure the proper alignment of the instruments, which bore through and are passed through the narrow pedicle. The availability of CAT scanning or sophisticated biplane fluoroscopy in surgical procedures is limited due to the additional cost associated with equipping surgical suites with the necessary equipment. Further, to protect against accidental damage to the spinal cord during the conventional transpedicular approach to the vertebral body, the patient is typically placed in a restraining device and stereotaxic procedures are used to guide the physician's drill and cannulae through the pedicle. Due to the extraordinary care and precision required in conventional vertebroplasty, the time needed to complete the surgery and the cost associated with the procedure can be extensive. Further, general anesthetic is not recommended due to the close proximity of the physician's instruments to the spinal cord and the associated need to communicate with the patient. This requirement, however, also causes concern of movement of the patient during the surgery; movement which could have serious consequences should the spinal cord be damaged as a result. Scholten et al. in U.S. Pat. Nos. 4,969,888 and 5,108,404 teaches the conventional surgical technique of vertebroplasty with the additional step of employing a balloon as an expansion device within the body of the vertebrae to compact the osteoporotic cancellous bone away from the center and against the walls of the vertebral body. This additional step to conventional vertebroplasty, taught by Scholten et al., is intended to provide additional space within the vertebral body to accept the flowable bone cement through the needle (syringe). While the conventional vertebroplasty technique using conventional surgical apparatus has the distinct disadvantage of drilling through the pedicle with the potential risk of damage to the spinal column, this additional balloon expander employed in the process of Scholten et al., provides an additional disadvantage by compressing the naturally present internal matrix of the osteoporotic vertebra against the wall of the vertebral body. Absent this natural matrix, the injection of bone cement into the cavity created by the compressing step results in the formation of an unstructured bolus of bone cement in the center of the vertebral body. Because of the compression of cancellous bone, which as a result lines the walls of the vertebra, the bone cement which is infused into the vertebral body does not make a strong, direct, bonding contact with the vertebral wall, thus resulting in a potentially weaker post-surgery vertebral body.

There is, therefore, a great need for a surgical technique and associated instrumentation by which osteoporotic bone can be safely, expeditiously and efficiently treated. There is a particular need for a vertebroplasty procedure and associated instrumentation which provide a safer, faster procedure that ultimately results in a repair to the osteoporotic vertebral body wherein the injected material does not disturb the natural matrix of the cancellous bone, which along with direct contact to the vertebral wall provides a strong, composite matrix. The present invention provides an apparatus and a method of percutaneous bone failure fixation, which satisfies these needs.

SUMMARY OF THE INVENTION

The process and apparatus of the present invention can be generally used to perform osteoplasty, that is the introduction of any injectable material into any of the bones or tissues of the body. The present invention is particularly suitable for injecting materials into bones which have or are susceptible to compression failure due to lesions within cancellous bone. More particularly, this invention relates to a method and apparatus, involving the injection of materials for the fixation of lesions or failures of bones, particularly as a result of osteoporosis, tumor, other pathogenic conditions or trauma. The invention is especially suitable for use in the vertebroplasty procedures, such as, the fixation or prevention of vertebral body compression failures, although the instrumentation and methods of the present invention can be used for a wide variety of osteoplasty procedures, such as, failures or lesions in bones throughout the body.

An object of the present invention is to provide an apparatus, which is useful for the surgical procedure of safely introducing a material into a lesion or space within or around a bone or tissue.

Another object of the present invention is to provide a surgical method for safely introducing an injectable material into a lesion or space within or around a bone or tissue.

More particularly, it is an object of the present invention to provide an apparatus, which is sized and configured to safely contact or breach the cortical bone and establish an introducing channel through the apparatus and through the cortical bone into the cancellous bone through which a material can be introduced. The material introduced into the interior of the bone can be any biocompatible or therapeutic materials, such as, for example, antibiotics, whole cellular implants, natural products of cells, recombinant nucleic products, protein products of recombinant cells, allograft or autograft bone, bone cement products as are well known in the art (such as polymethylmethacrylate and the like), or any other flowable material useful for therapeutic, prosthetic, or bone strengthening purposes.

Another object of the present invention to provide an apparatus, which is sized and configured to be used by a physician to safely introduce a material into the cancellous bone of a vertebral body. In the surgical procedure of the present invention the apparatus can introduced by direct vision, open or percutaneously, laproscopically, thorascopically, or by open surgical procedures. The apparatus can be introduced into the vertebral body by a variety of approaches, to include, for example, postero-lateral and lateral and/or bilateral percutaneous approaches and a transpedicular approach. Such introduction of the apparatus can be accomplished with or without the conventional requirement for CAT scanning or sophisticated biplane fluoroscopy and further can be performed safely using general or local anesthetic. Introduction of the apparatus can be facilitated by use of indicia disposed on the guide wire, the cannulae or both, which are part of the apparatus. The indicia can be radioopaque or radiotranslucent. No irrigation, evacuation, or use of cancellous bone expanders is required for the successful use of the apparatus to introduce the material into the interior of the vertebral body.

Additionally, an object of the present invention is to provide a modular pedicle finder, which facilitates the placement of an instrument for penetrating the pedicle of a vertebra.

BRIEF DESCRIPTION OF THE DRAWINGS

The invention will now be described, by way of illustration only, with reference to the accompanying drawings.

FIG. 5 is a depiction of a guide wire that can be used in the present invention having a Luer lock for providing a fluid tight attachment to an infusion device, syringe or handle.

FIG. 6 is a depiction of a delivery cannulae that can be used in the present invention, which is configured to be capable of receiving the guide wire shown in FIG. 5.

FIG. 7 is a depiction of the assembled guide wire and delivery cannulae shown in FIGS. 5 and 6.

FIG. 8 is a depiction of a handle configured to be capable of removable attachment to the Luer lock of the guide wire shown in FIG. 5 or the cannulae shown in FIG. 6.

FIGS. 9A, 9B and 9C are detail views of the handle shown in FIG. 8.

FIGS. 9G–9H depict a cannulated T-handle which can be used with the present invention. FIG. 9I is a partial sectional view of an alternative embodiment of the present invention employing a handle having a removable proximal end, which acts an extended impact surface.

FIGS. 10D–10J are various views of an alternative embodiment of a plunger that can be used with an embodiment of the present invention employing a threaded plunger and cannulae. FIG. 10K shows a mixing tip option which can be employed with the present invention.

FIGS. 11C–11E are depictions of an alternative multilumen-type cannulae which can be used to contain more than one material for simultaneous or sequential injection in the method of the present invention.

FIGS. 13A–13B show a specialized impact forceps, which can be used with the device of the present invention for purpose of facilitating the entry of the device into the bone.

FIG. 14. shows a transpedicular approach to the vertebral body. FIG. 15 shows the deep penetration of the vertebral body using a transpedicular approach.

FIG. 22 is a depiction of a hand operated syringe gun shown in assembly with a delivery syringe tube, which can be used with the present invention.

DETAILED DESCRIPTION

The apparatus and method of the present invention can be adapted for use in the introduction of any material into any bone that contains a lesion or sufficient porosity to accept the materials. The employment of the apparatus and surgical procedure of the present invention in vertebroplasty; particularly to treat vertebral compression failures which result from osteoporotic conditions is herein described below as illustrative of the present invention.

Figure 1:
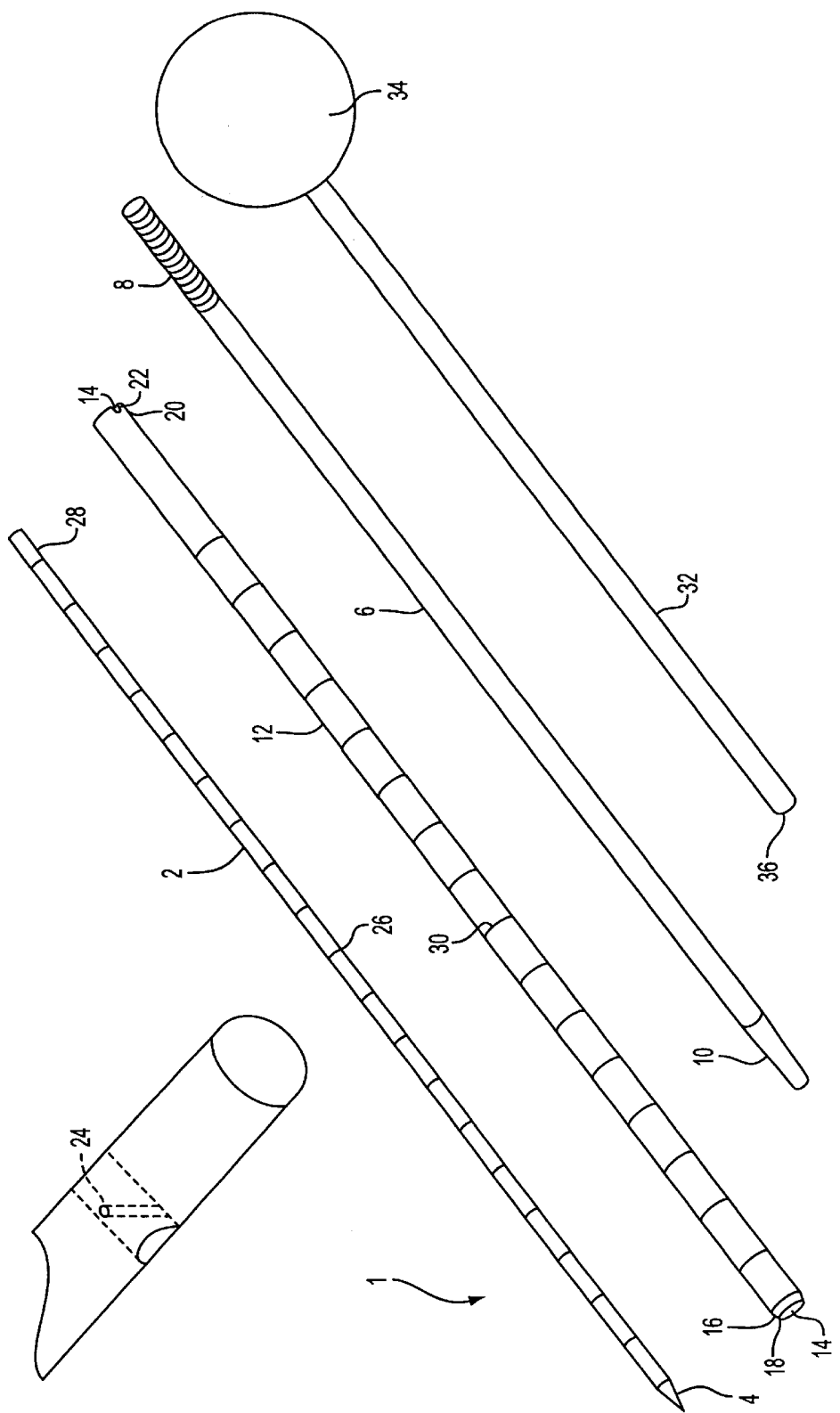
FIG. 1 is an isometric view of the components of the one embodiment of the apparatus of the present invention.
Figure 2:
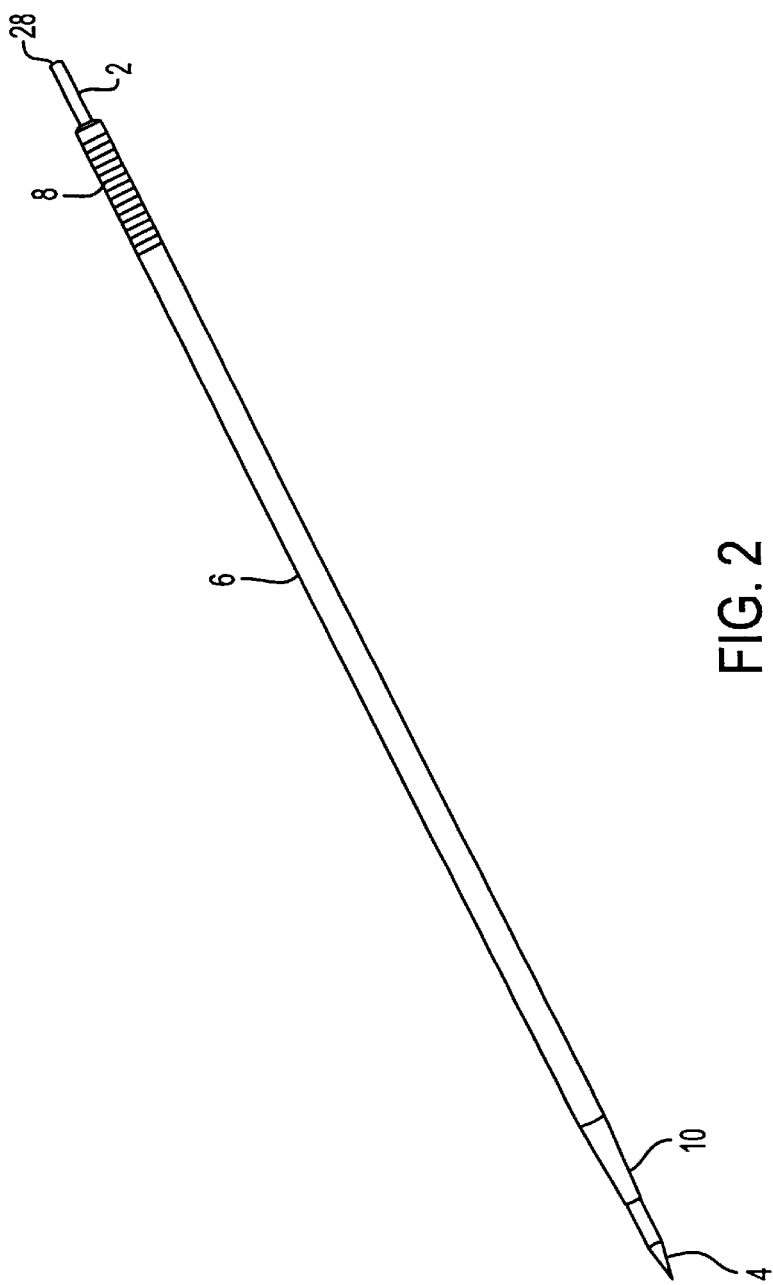
FIG. 2 is an isometric view of the assembled Guide wire and Aligning Cannulae of the present invention.
Figure 3:
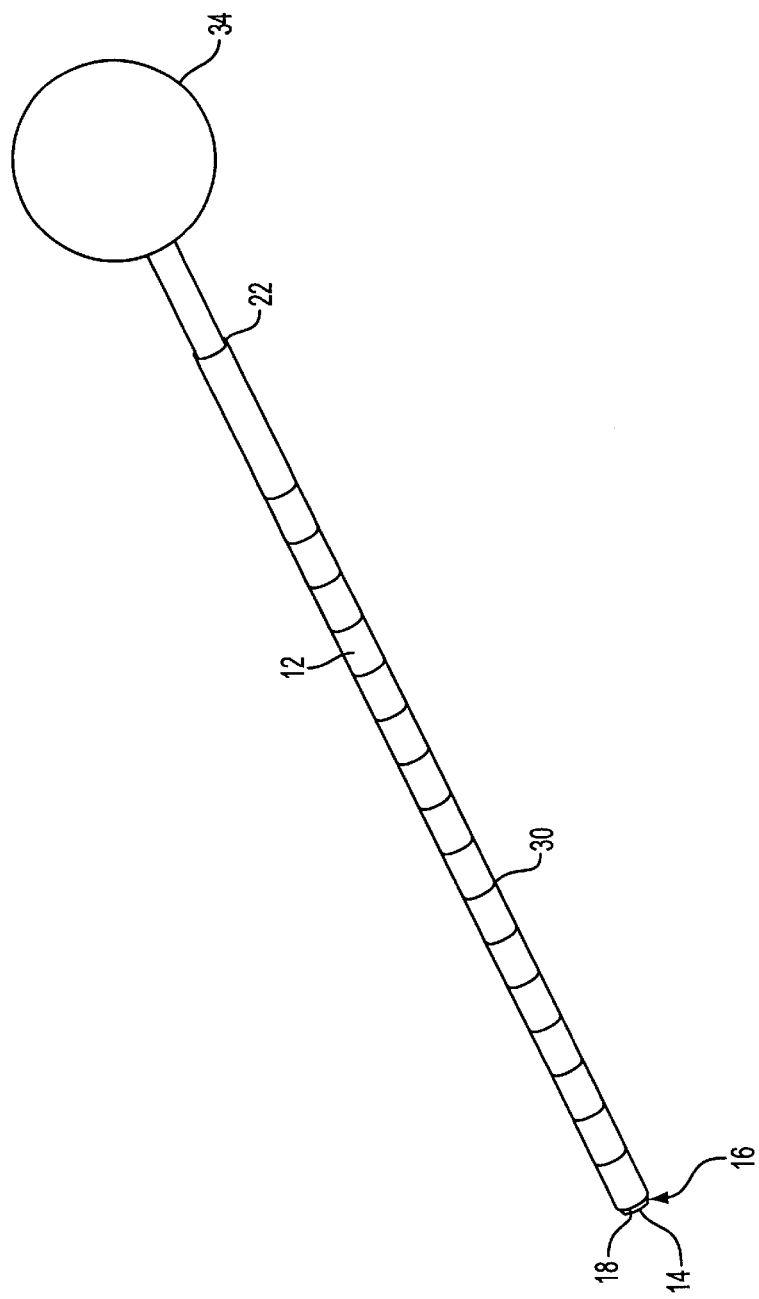
FIG. 3 is an isometric view of the assembled Delivery cannulae and Plunger of the present invention.

The following description of the device of the present invention relates to FIGS. 1–3. The apparatus of the present invention is an intraosseous injection device generally shown at 1. One object of the present invention is to use the injection device I in a surgical procedure for the safe, effective introduction of materials into a lesion within a bone, whereby the procedure includes the introduction of a first guide wire 2 having a tapered end 4 for effectively breaching the dense compact bone, for example, the cortical bone of the vertebra. An aligning cannulae 6 is configured and sized to easily pass over the first guide wire 2 and when passed down the shaft of the guide wire 2 serves as a soft tissue protective sleeve from the point of entry of the apparatus into the body to the contact point at the exterior surface of the bone being treated. The aligning cannulae 6 has a blunt first end 8 which has a textured surface to facilitate handling and a tapered second end 10 which during operation of the instrument is brought into contact with the bone being treated.

A delivery cannulae 12, which is sized and configured to easily pass over the aligning cannulae 6 is inserted over the aligning cannulae 6 for purpose of providing a material conduit 14 through which the injectable material can be introduced into the bone being treated. The delivery cannulae 12 is configured at the delivery cannulae distal end 16 to have a securing edge 18 which serves to hold the delivery cannulae 12 in place on the outer surface of the bone being treated. The delivery cannulae proximal end 20 is configured to have a handle retention member 22, which serves to releasably secure a handle member 24 to the delivery cannulae 12. The handle member 24 can be used for insertion of the delivery cannulae 12 over the aligning cannulae 6 and for improving the grip of the user when placing the securing edge 18 of the delivery cannulae 12 firmly into position on the outer surface of the bone being treated. The removable handle member 24 also can be useful at a later step of the surgical procedure for providing a secure grip, which may be necessary to disengage the delivery cannulae 12 from the surface of the bone prior to extracting the device 1 from the body of the patient. The surface of the delivery cannulae can be provided with graduated indicia 30 which provide depth of penetration information during insertion by the user. The cannulae can be configured such that the cannulae is primarily radiotranslucent with portions being radioopaque to provide indicia along a portion of the entire length of the cannulae. The indicia can be equally disposed along the length of the cannulae, can be disposed in a graduated increasing or decreasing scale, or can be a combined arrangement whereby some portion is of equal graduations and some portion is of sliding increasing or decreasing graduations. It is also within the concept of the present invention to provide a radioopaque cannulae having portions, which are radiotranslucent to provide indicia. One aspect of the present invention is to include a radioopaque distal end of the cannulae to enable precise determination of the location of the distal end during operation of the device. The radioopaque indicia can be made radioopaque by any means known in the art to include the use of gold or other metals.

The guide wire 2 can be provided with graduated guide wire indicia 26 which extend from the tapered end 4 to the more proximal guide wire blunt end 28. The guide wire indicia 26 provides a means by which the user can easily determine the depth of insertion of the guide wire 2 into the patient during the surgical procedure of the present invention. The guide wire indicia can be arranged in an equal distribution along the length of the guide wire or can be distributed in increasing or decreasing graduation or a combination thereof.

A plunger member 32 can be provided with an ergonomically configured gripping member 34 at a first end which is used by the user to exert pressure on the plunger member 32 as it snuggly passes through the material conduit 14 of the delivery cannulae 12. The second end of the plunger member 32 is configured to have a blunt smooth tip 36. The fit of the plunger member 32 within the material conduit 14 of the delivery cannulae 12 is such that easy sliding engagement of the plunger is permitted without allowing the passage of the injectable material proximally past the blunt smooth tip 36. Further, the plunger member 32 is sized diametrically to provide a fit within the material conduit 14 so as to permit the release of air proximally past the plunger while maintaining the PSI of the injected material as the plunger forces the material distally through the outer cannulae and into the subject. The user can, upon exerting force against the gripping member 34, displace the plunger member 32 through the length of the material conduit 14 of the delivery cannulae 12 and, in doing so, displace any preloaded injectable material out of the distal end of the material conduit 14, through the breach formed by the tapered end 4 of the guide wire 2 and into the interior of the bone being treated.

Figure 4:
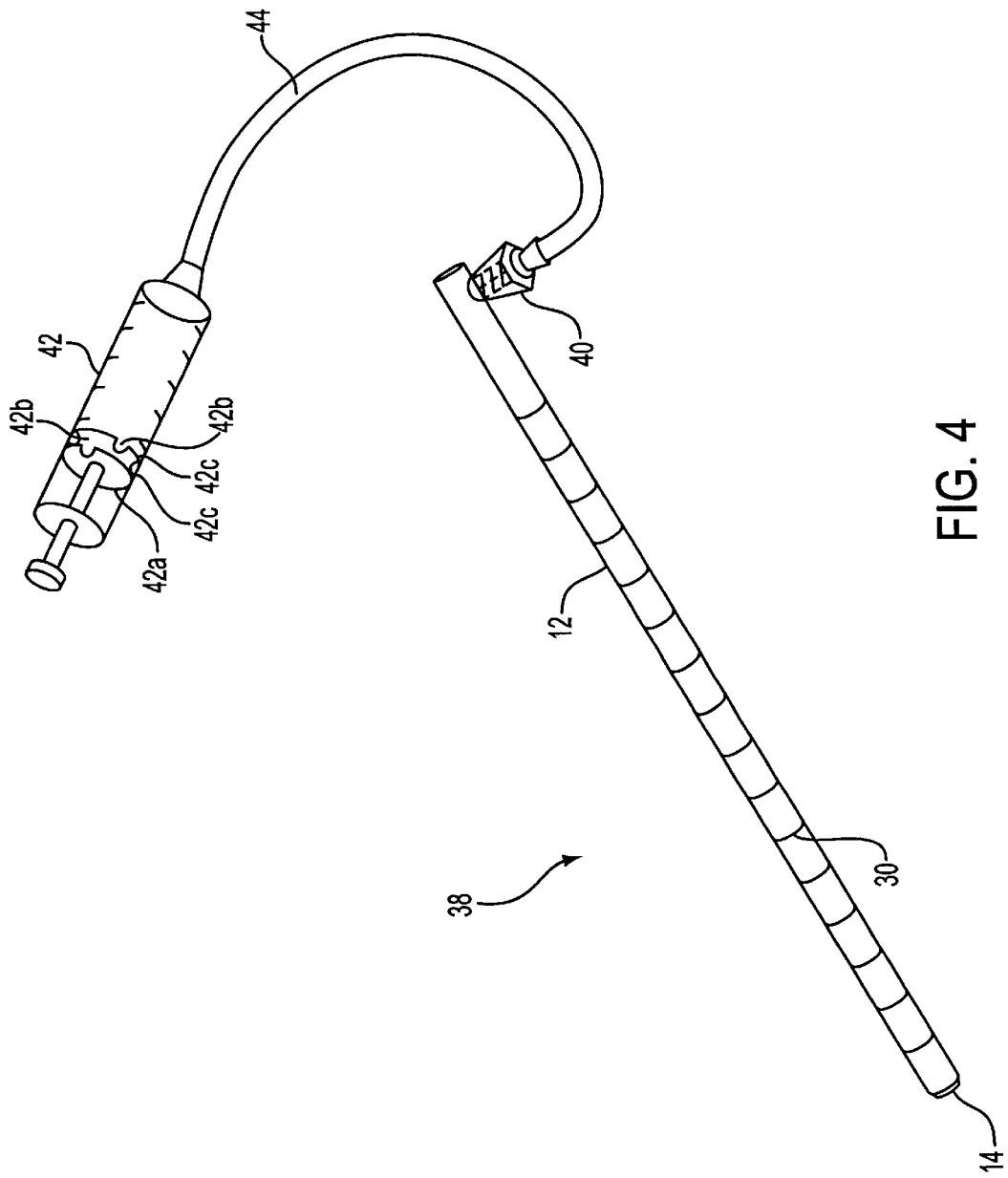
FIG. 4 depicts the present invention equipped with an optional syringe system.

Alternatively, the movement of the material through the material conduit 14 and into the cancellous bone of the vertebrae could be accomplished by means of a syringe system, generally shown in FIG. 4, at 38. The syringe system of the present invention can include a fluid connector 40, such as, for example, a conventional Luer lock, a bayonet fitting, a hydraulic quick disconnect fitting, or any other fluid tight fitting as is well known in the art. The fluid connector 40, which would be attached to the delivery cannulae 12 and in fluid tight communication with the material conduit 14 can be attached directly to a syringe 42, to a syringe via a flexible conduit 44, or alternatively to an automated infusion device as is well know in the art (not shown). The syringe system 42 can be provided with a syringe plunger tip 42*a*, which can include one or multiple sealing rings diametrically sized to slidably move within the syringe 42 in a manner conventional to syringes but with one or more air passages 42*b* to allow the proximal flow of air past the plunger tip 42*a* while the plunger tip 42*a* forces the material distally through and out of the syringe 42*a*. The air passages 42*b* are sized to permit the flow of air but not the flow of the injectable material in a proximal direction within the syringe 42. Further, the air passages 42*b* can be arranged on one or more than one annular rings 42*c* on the plunger tip 42*a*. When multiple air passages 42*b* are arranged on multiple annular rings 42*c*, it is preferred that the air passages 42*b* through one annular ring 42*c* are offset from the air passages 42*b* from an adjacent annular ring 42*c* The fluid connector 40 can be attached to the delivery cannulae 12 in approximate alignment to the longitudinal axis of the delivery cannulae 12, at right angles to the longitudinal axis of the delivery cannulae 12, or at any position or any angular arrangement to the delivery cannulae 12, which will permit fluid flow through the connector into the material conduit 14.

In the process of the present invention, the mixing of the injectable material, such as bone cement, could be accomplished within the syringe system.

Another alternative mode of operation would permit the movement of the plunger can be automated by attachment of an electromechanical or pneumomechanical servo mechanism which would be under control of the physician.

Without departing from the concept of the present invention presented in FIGS. 1–4, alternative embodiments of the intraosseous injection device and peripheral elements as shown in FIGS. 5–12B can be provided for use in the method of the present invention.

As best shown in FIG. 5, a locking guide wire 46, having an attached longitudinally aligned male Luer lock 48 and female Luer lock 50 can be provided for use with a corresponding alternative delivery cannulae 52, the locking guide wire having corresponding guide wire connectors 54. FIG. 7 shows the alternative delivery cannulae 52 assembled with the locking guide wire 46. FIG. 8 shows a locking guide wire handle 56, which can be secured to the locking guide wire by the Luer lock 48.

As best shown in FIGS. 9A–9C, the locking guide wire handle 56 defines a longitudinal lumen 58, which is sized and configured to permit passage of the locking guide wire 46 as well as the larger cross dimension diameter of the delivery cannulae 52. The guide wire handle 56 can be provided with a view slot 60, which may be equipped with a magnifying or non-magnifying clear cover (not shown). The viewing slot 60 is sized and configured in the guide wire handle 56 to permit the user to view the graduated guide wire indicia 26 during operation of the present invention. The ability to view the guide wire indicia 26 during operation of the present invention provides a safety feature, which permits the operator to know the depth of insertion of the subsequently positioned aligning cannulae and/or outer cannulae. The guide wire handle 56 can define a first clearance hole 62, which provides cross access to the 10 longitudinal lumen 58 and has an orifice diameter sized and configured to correspond to the guide wire 46 and can be used to help drive the aligning cannulae into position. The guide wire handle 56 can be similarly configured to define a second clearance hole 66, which serves much the same function as the first clearance hole with the exception that the second clearance hole is sized and configured to assist in the insertion of the large delivery cannulae 52. The impact connector element 64 can be provided in cross-sectional diameters, which correspond to either the first clearance hole 62 or the second clearance hole 66. The handle distal end 68 can be provided with a handle Luer connector 70 which corresponds to connectors 54 of the alternative delivery cannulae 52, thus providing a secure, quickly released connection between the guide wire handle 56 and the alternative delivery cannulae 52. An enlarged cross-sectional view of the handle Luer connector 70 is shown in FIG. 9B. Although the Luer type connection disclosed in detail is the preferred means of providing the handle connection described above, it is within the concept of the present invention to provide the handle connection using any known connection means, such as, for example, other threaded connections, snap-fit connections, cotterpin connections, friction connections, and the like.

The locking guide wire 46 in combination with the attached guide wire handle 56 and the alternative delivery cannulae 52 provides a very effective modular pedicle finder which can be used to facilitate the location and penetration of the pedicle of a vertebra. The advantageous use of the alternative delivery cannulae 52 in combination with such a modular pedicle finder provides the user with a device accessing the vertebral body by a transpedicular approach far superior to that known in the art. The positioning and direction of insertion of the guide wire 2, or locking guide wire 46 can be facilitated by using image guidance means such as fluoroscopy, CAT scan, MRI or the like. Stereotactic methods and the employment of registration diodes can also be employed to provide accuracy in guide wire insertion when the process of the invention is practiced from any approach to the vertebral body, including the use of the locking guide wire 46 to perform a transpedicular approach to the vertebral body. It is also within the concept of the present invention to employ robotic systems to control the accuracy of the insertion of the device.

Figure 9D:
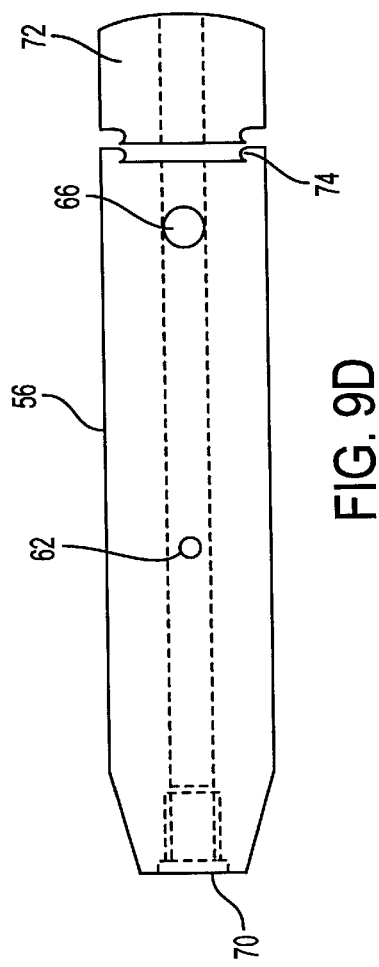
FIG. 9D is a depiction of an embodiment of the handle shown in FIG. 8 which is configured with a removable proximal end for purposes of exposing the proximal end of the guide wire for ease in movement, insertion, and extraction from the delivery cannulae.
Figure 9F:
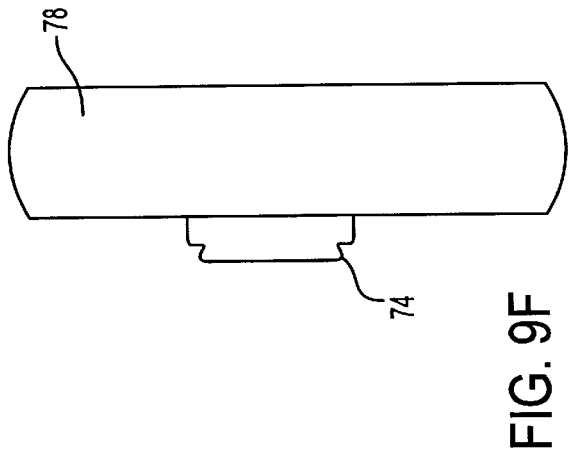
FIGS. 9E–9F shows examples of some of the alternative end attachments, which can be employed with the handle shown in FIG. 9D.
Figure 9E:
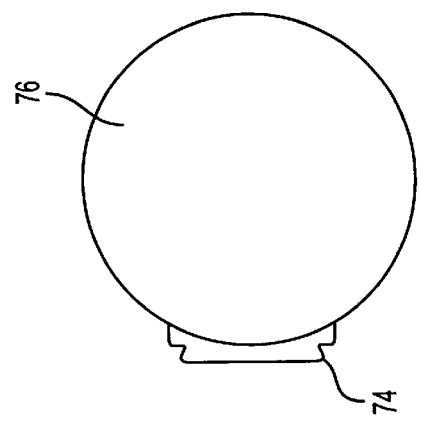

As best shown in FIG. 9D, one alternative embodiment of the guide wire handle 56 can be provided with a removable proximal end 72. The removable proximal end 72 permits the user to expose the proximal end of the guide wire for ease in movement, insertion, and extraction from the delivery cannulae. The removable proximal end 72 of the guide wire handle 56 can be releasably secured to the guide wire handle 56 by any known releasable connection means, such as, for example, threaded connections, snap-fit connections, cotter-pin connections, friction connections, and the like. FIGS. 9E–9F show examples of some of the alternative end attachments which can be employed with the alternative embodiment of the guide wire handle shown in FIG. 9D. Any configuration for the removable proximal end 72 that provides a gripping surface for the user is within the concept of the present invention. Preferred alternative embodiments of the removable proximal end 72 are the spherical or oval gripping surface 76 (FIG. 9E) and the T-handle form 78

(FIG. 9F). Alternative handles which can be used with the present invention includes the cannulated T-handle shown in FIGS. 9G–9H. FIG. 9I provides a partial sectional view of one embodiment of the present invention utilizing another option for the removable proximal end 72, that of a removable impact extension member 72*a* This optional member enables the user to attach an impact surface which surrounds and protects the guide wire if impacting the device is necessary during operation.

Figure 10B:
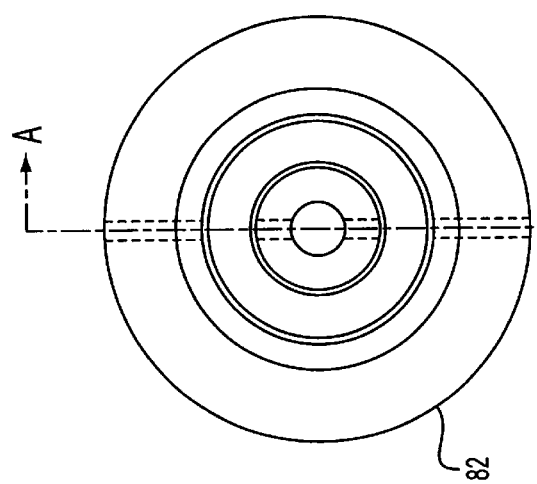
FIGS. 10A–10B are cross-sectional side (10A) and end (10B) views of the plunger shown in FIG. 10C, which can be used with the apparatus of the present invention.
Figure 10A:
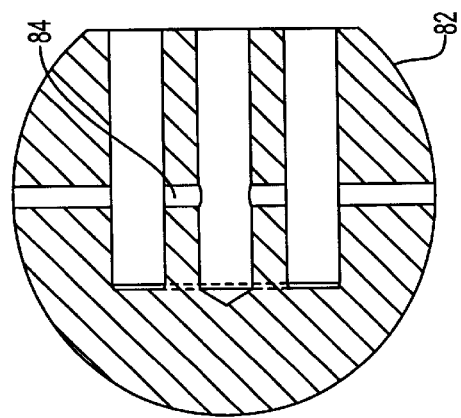
Figure 10C:
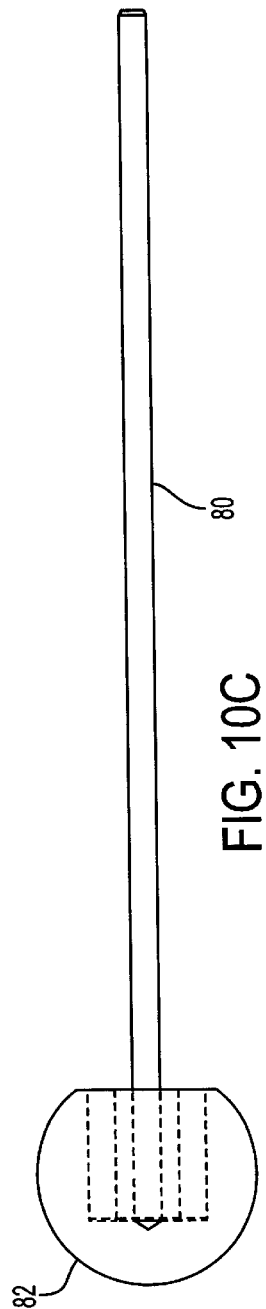
FIG. 10C is a depiction of the plunger assembly, which includes the handle shown in FIGS. 10A–10B.

FIGS. 10A–10C show details of an alternative plunger assembly 80 which can have a removable gripping member 82, which is secured by a removable lock pin 84 or similar securing member. The alternative plunger assembly 80 with the gripping member 82 removed can be configured to an automated impelling means (not shown) much like automated infusion devices, which are known in the art. With the alternative plunger assembly 80 so configured, the degree of pressure applied to the plunger assembly in moving the material through the material conduit can be automatically controlled by the user to avoid over pressurizing the material into the spaces within the bone. The plunger assembly can be manufactured with a lock pin 84, which is not removable. So configured, the plunger assembly would essentially be that of the earlier described unitary plunger member 32.

Figure 10H:
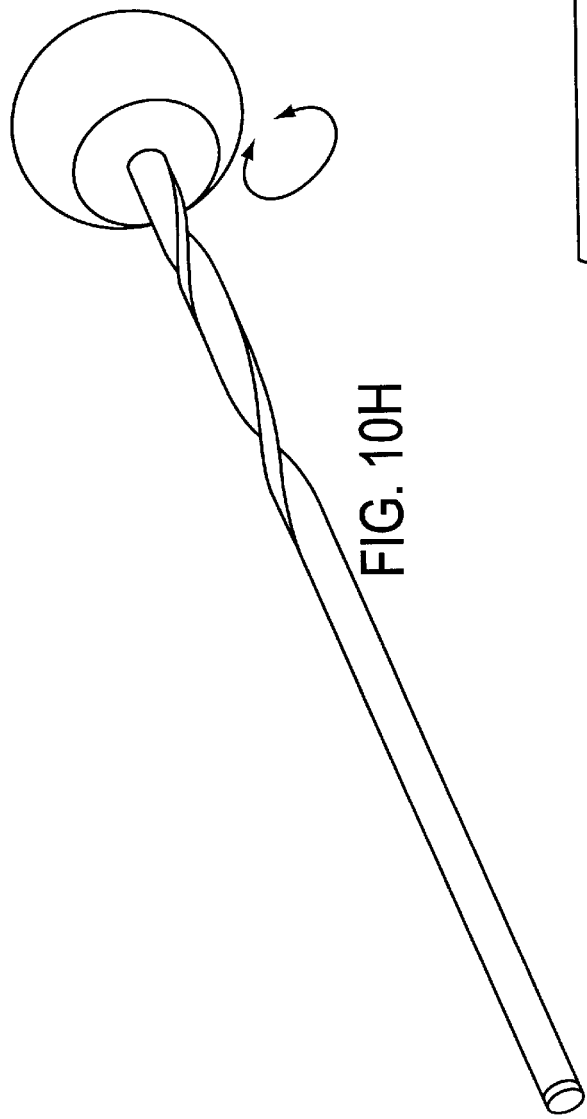
Figure 10I:
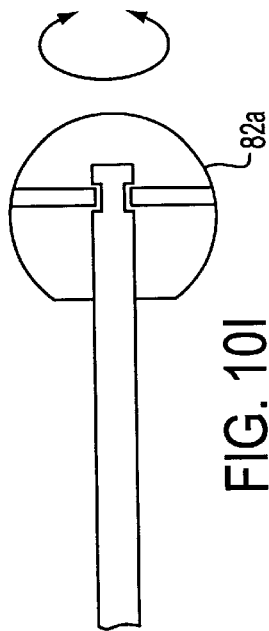
Figure 10J:
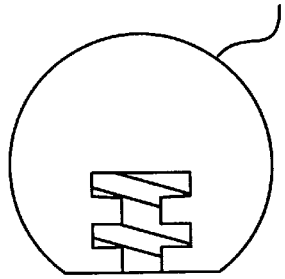

FIGS. 10D–10J provide depictions of alternative embodiments of the present invention, which can use a standard threaded plunger and cannulae (FIGS. 10D–10E) or, as shown in FIGS. 10F–10G a long-threaded or optional mixing-tip plunger (FIG. 10K). Such embodiments of the present invention provide a controlled insertion of the plunger and an inherent resistance to any back pressure from the material being injected through the device. FIGS. 10H–10J depict alternative handles which can be used with any of the earlier described embodiments of the present invention; particularly those shown in FIGS. 10D–10G. The swivel ball gripping member 82*a* can be used to provide ease of movement of the plunger; particularly one of the threaded plungers depicted in FIGS. 10D–10G.

Figure 11A:
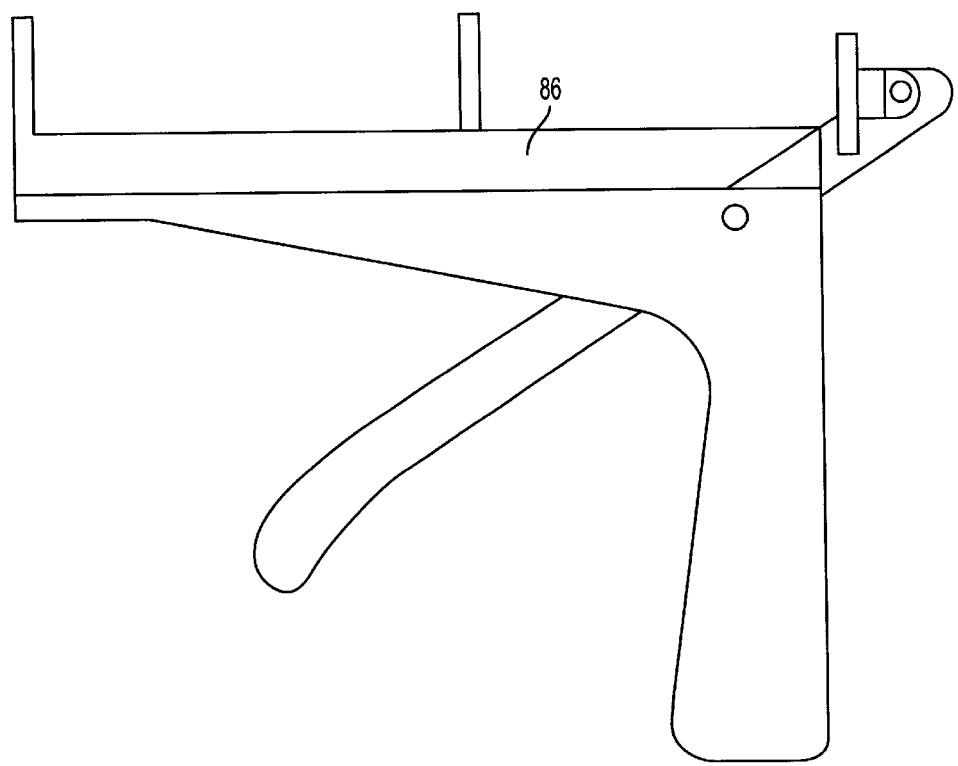
FIG. 11A is a depiction of a hand operated plunger actuator which can be used with the apparatus of the present invention.
Figure 11B:
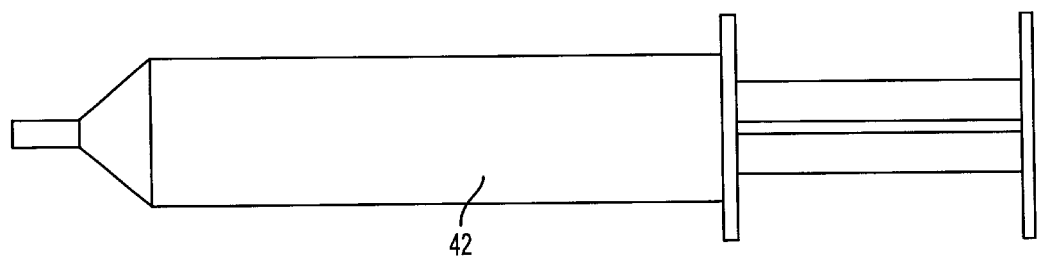
FIG. 11B is a depiction of a type of syringe which can be used to contain a material for use in the method of the present invention, the syringe being an example of the type syringe which can be used with the hand operated plunger actuator shown in FIG. 11A. Unlike other plunger actuators, this plunger actuator of the present invention allows for controlled injection down to 1 cc of material per squeeze by the operator.

FIG. 11A shows a hand operated plunger actuator 86, which can be used to assist in the impelling of the material through the material conduit 14 of the present invention. FIG. 11B shows a type of syringe 42 which can be used to contain the material for use in the method of the present invention, the syringe being an example of the type syringe which can be used with the hand operated plunger actuator shown in FIG. 11A. Other impelling devices can also be used to assist in the movement of the material into the material conduit 14 without departing from the concept of the present invention.

The present invention also contemplates the use of an intraosseous injection device similar to the embodiments described above with the alternative modification of providing lumens which incorporate rifling along the bore of the lumen which can be of assistance to the user in enabling the ease of material insertion and allowing the escape of air or other fluids of less consistency than that of the material being infused into the body. The tolerances between the plunger assembly 32 or 80 and the sides of the material conduit 14 are such that the material is easily forced through the conduit without loss of the material around the plunger, yet air or other light consistency fluids within the material conduit 14 are allowed to pass away from the body around the plunger to freely escape.

It is also within the concept of the present invention to provide an intraosseous injection device which has multiple lumens for passage of the material into the body, thus allowing for the possibility of mixing of material components at the time of injection. A multi-lumen device 116 such as that shown in FIGS. 11C–11E can be used in a variety of situations, to include, for example, when it is desirable to withhold mixing of injectable material components as long as possible prior to injecting the mixed components into a subject. As best shown in FIG. 11E, the device can be provided with a separate plunger 118*a*, 118*b* for each lumen; the plungers being configured such that they can be operated independently or can be operated together by apply pressure to the overriding handle of one of the plungers 118*a*.

Figure 12A:
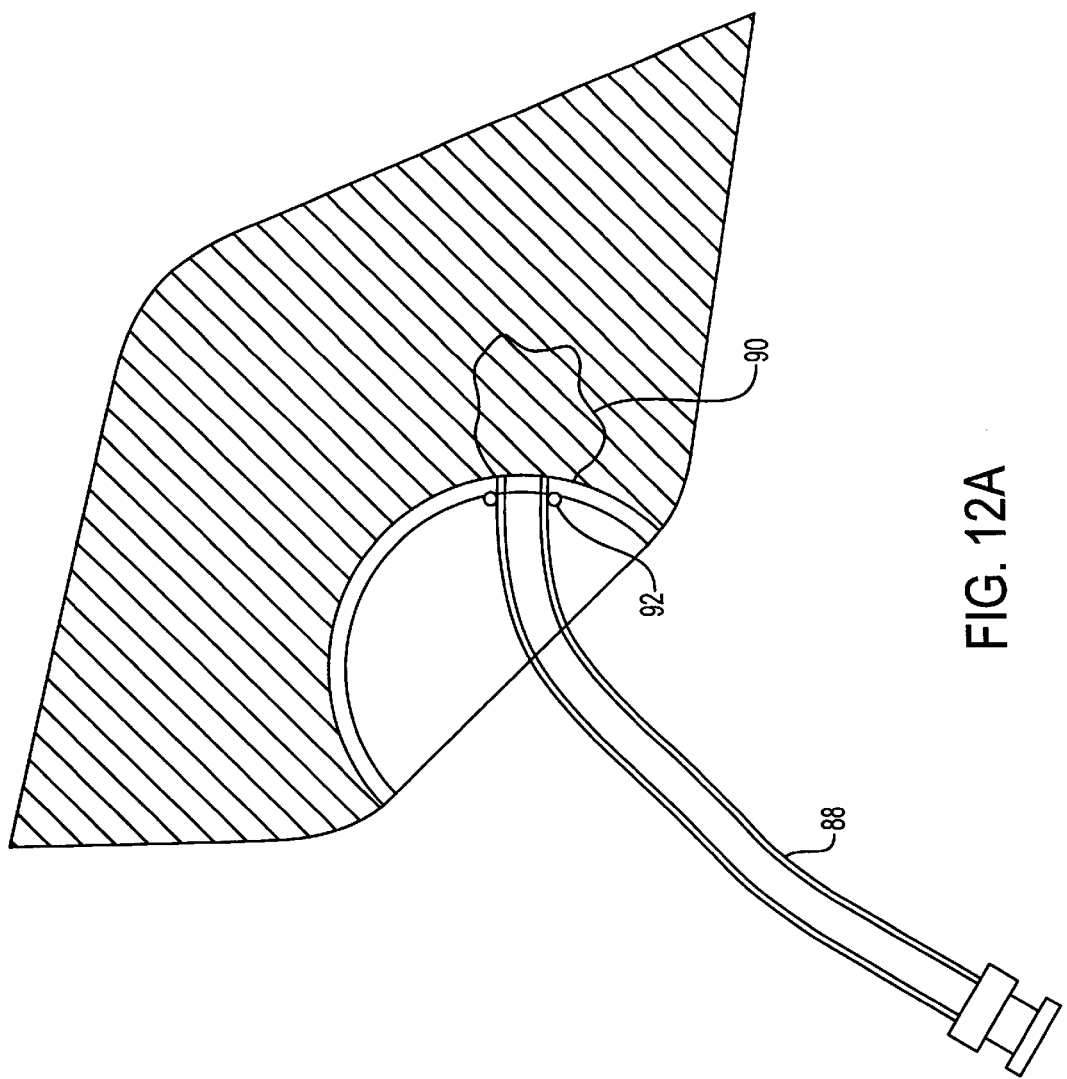
FIG. 12A is a depiction of an application of the method of the present invention, which employs a flexible cannulae for delivery of a material into the bone material of a joint, such as, for example into the acetabulum.
Figure 12B:
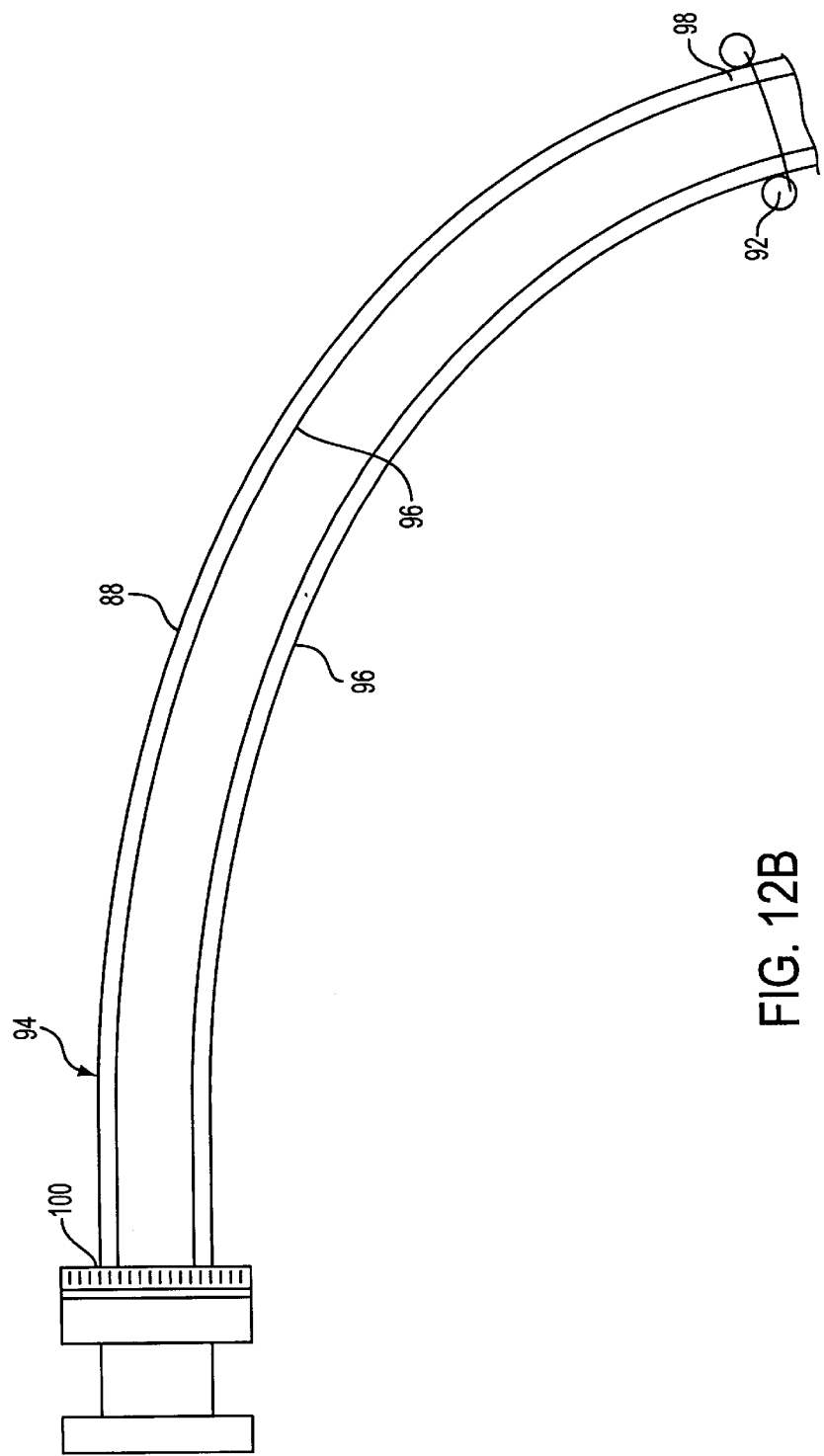
FIG. 12B is an enlarged cross-sectional depiction of the flexible cannulae shown in FIG. 12A showing an example of a mechanism which can be employed to steer the flexible cannulae. The plunger technology depicted in FIG. 10 maintains a flexible shaft for delivery through the flexible lumen of the flexible cannulae.

FIG. 12A shows an application of the method of the present invention, which employs a flexible delivery cannulae 88 for delivery of a material into the bone material of a joint, such as, for example into the acetabulum 90. A sealing washer 92 can be provided to assist in maintaining the delivery cannulae 88 in place at the point of entry into the bone. FIG. 12B is an enlarged cross-sectional depiction of the flexible cannulae shown in FIG. 12A showing an example of a mechanism which can be employed to steer the flexible delivery cannulae 88. FIG. 12B depicts a steering wire system 94, which employs at least two steering wires 96, one end of each steering wire being attached at the delivery cannulae distal end 98 in opposition one to the other and the other end of the respective steering wires being attached in opposition one to the other to a rotary reel control 100 located adjacent to the Luer lock of the delivery cannulae. The steering wire system 94 described herein and shown in FIG. 12B is provided as an example of a steering system which can be used in the present invention. It is, however, within the concept of the present invention to employ any of the known means of producing a steerable catheter.

Also provided is a specialized impact forceps 102, as shown in FIGS. 13A–13B. The specialized impact forceps can be used in conjunction with the device of the present invention for purpose of facilitating the entry of the device into the bone. The impact forceps 102, are operated by a user much like surgical forceps known in the art. A hinge member 104 connects the opposing halves 106*a* and 106*b* of the forceps allowing the halves 106*a* and 106*b* to be closed tightly together. A forceps lock 108 allows the halves 106*a* and 106*b* to be locked into a closed position. Unique to the specialized forceps of the present invention is a first groove 110 and a second groove 112 found in the end of the forceps which is tightly closed when the forceps is in the closed and locked position. The first groove 110 is sized and configured to securely grasp the guide wire element 2, which is sized to fit the first clearance hole 62 of the guide wire handle. The second groove 112 is sized and configured to securely grasp an impact connector element 64, which is sized to fit the second clearance hole 66 of the guide wire handle. The forceps 102 can have a striking plate 114, which is configured to receive driving blows from an operator using a mallet, hammer, springloaded driver, or other impacting device. In combination, the forceps 102 and the first clearance hole 62 can be used to facilitate driving the guide wire 46 into position in the bone. Similarly, the forceps 102 and the second clearance hole 66 can be used to facilitate driving the delivery cannulae into position.

In its most general form, the surgical procedure of the present invention includes the step of the physician, by tactile sensation, recognizing the appropriate back-pressure on the plunger gripping member and thereafter ceasing the manual introduction of injectable material into the cancellous bone. It is, however, within the scope of the present invention to provide a back-pressure sensor attached to the device 1 such that when the preselected back-pressure on the plunger member is reached, the physician is apprised of the situation and introduction of material can be discontinued. It is further, within the scope of the present invention for the alternative embodiment which provides for automatic infusion of the biomaterial through the device 1, to provide a processor which receives a back-pressure signal at a preselected back-pressure and in turn transmits a pressure cut-off signal to the automatic infusion system.

The injection device of the present invention can be fabricated from any of a variety of materials, which are compatible for use as surgical instruments. Examples of such materials include metallic materials and non-metallic materials, which are suitable for use in surgical instrument manufacturing processes. Metallic materials can include, for example, surgical instrument grade stainless steel and alloys thereof, anodized aluminum and alloys thereof, and titanium and alloys thereof to include nickel-titanium. Non-metallic materials can include, for example, thermoplastics, ceramic materials, carbon fiber materials, composite materials, and the like. Portions of the device which are radioopaque can be constructed or coated with any radioopaque material, to include but not limited to gold or other metals.

It is within the scope of the present invention to provide a kit, which includes the injection device disclosed above. The kit could also include some or all of the alternative features discussed herein, to include the injectable material. Such a kit could be provided in an appropriate packaging, which could be designed for autoclaving or other means of sterilization.

In operation, the user can insert the guide wire 2 using a posterior lateral approach to the vertebral body. This can be safely done with the patient under general or local anesthetic.

The surgical procedure of the present invention can be performed by direct vision, open or percutaneously, laproscopically, thorascopically, or by open surgical procedures. Performance of the surgery percutaneously is preferred. A very important feature of the present invention is the ability to perform the surgical procedure percutaneously by a posterior-lateral approach in addition to the transpedicular approach. The use of a posterior-lateral approach is preferred over the transpedicular approach because the physician can quickly, effectively and, most importantly, safely perform a vertebroplasty without bringing any instruments within close proximity to the spinal cord. Alternatively, the method of the present invention can be performed using a transpedicular approach with the limited bone penetration and accuracy of employment aspects of the present invention providing improved safety over conventional transpedicular approaches.

The surgical procedure is also easily adapted to be performed on any vertebrae from T3 down, which also represents a major expansion of applicability over the convention methods used.

Additionally, the procedure has been shown to be useful in fixing vertebral bodies which have tumors to the extent that the tumors have not caused the formation of holes in the compact bone of the vertebrae adjacent to the spinal cord.

Figure 14:
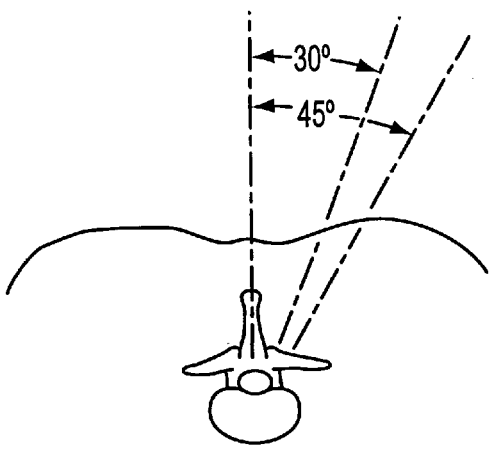
FIG. 14 and FIG. 15 are depictions of a conventional prior art method of vertebroplasty.
Figure 15:
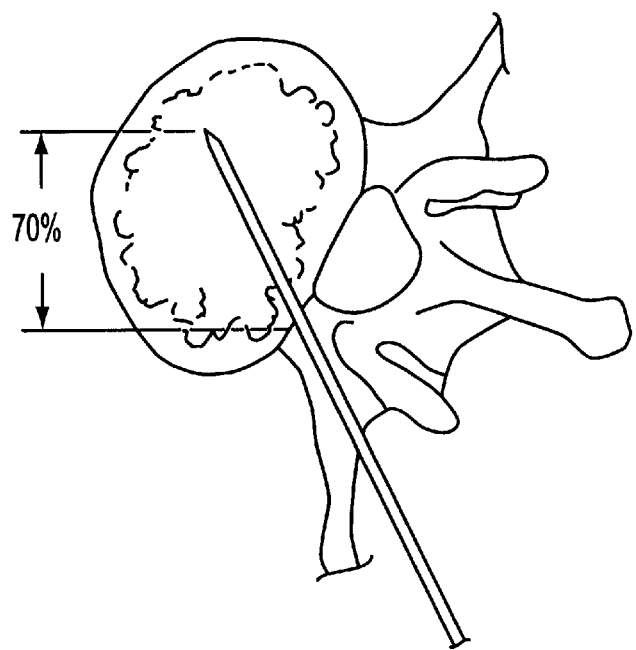

Of major importance is the very limited degree of penetration of the guide wire 2 through the compact bone of the vertebrae. Unlike conventional vertebroplasty, which requires CAT scanning to precisely control drilling using a conventional vertebroplasty apparatus through the pedicle (see FIG. 14 and FIG. 15), the present invention can be more efficiently, and more quickly accomplished being aided only by the use of fluoroscopy. FIG. 14, shows the angle relative to the spinal column for transpedicular approaches using the conventional vertebroplasty apparatus and the conventional procedure of deeply penetrating into the cancellous bone of the vertebral body. The preferred posterior-lateral approach to the vertebra by the guide wire 2 and the penetration of the tapered end, which need only penetrate the compact cortical bone of the vertebral body, results in the cancellous bone of the vertebra being left in tact. In the alternative transpedicular approach of the present invention the transpedicular approach angle is similar to conventional methods, however, the improved control of depth of penetration of the apparatus of the present invention provides greater accuracy and therefore greater safety over conventional apparatus and methods. It is well known in the art, as evidenced by the discussion in Gray's Anatomy, 38th Ed. (1995) at page 427 and 454, that the relatively thin-walled exterior compact bone derives powerful support from the trabeculae of cancellous bone located within. Conventional vertebroplasty drills through and penetrates well into the cancellous bone of the vertebrae (see FIG. 15), thus severely disrupting the natural internal reinforcing structure of the vertebra. In the preferred embodiment of the present invention the guide wire 2 does not penetrate through the cancellous bone and therefore does not radically disrupt the trabeculae of the cancellous bone. The result is that when the bone cement is introduced through the material conduit 14 of the delivery cannulae 12, it flows into the naturally porous configuration of the intact cancellous bone thus taking advantage of, not replacing, the natural internal supporting trabeculae structure of the vertebra.

Figure 16:
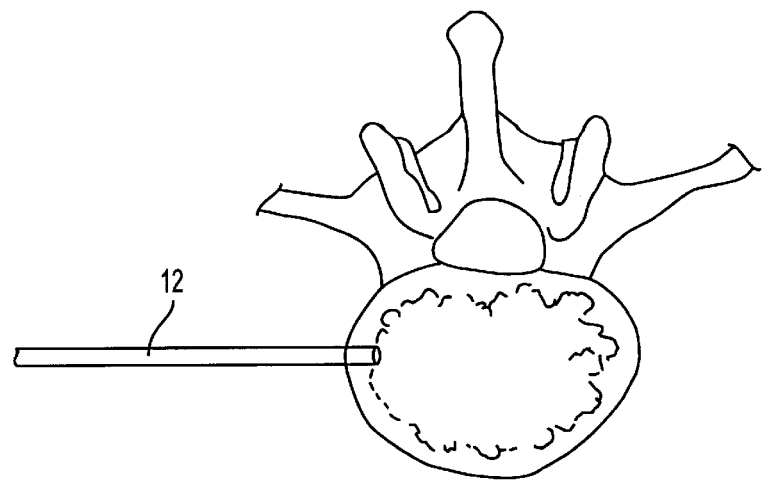
FIG. 16 is a depiction of the apparatus of the present invention positioned relative to a sectional view of a vertebral body during operation of the method of the preferred embodiment of the present invention.

As depicted in FIG. 16, In a first embodiment of the process of the present invention the vertebra are infused with bone cement using an entry port on one side only of the vertebra. This unilateral infusion process does not completely fill the porous structure of the natural matrix of the cancellous bone; but fills it sufficiently on one side to fully support the failed vertebra.

Figure 17:
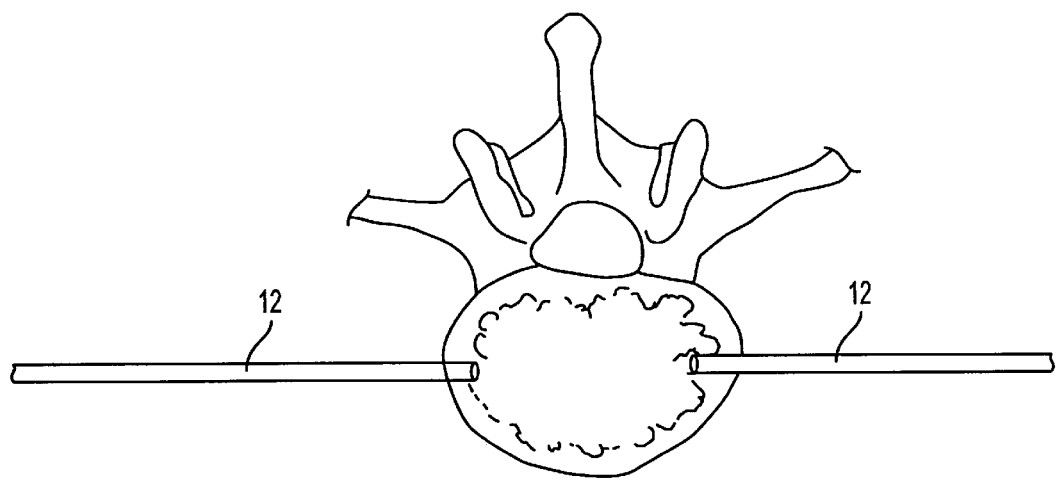
FIG. 17 is a depiction of a first alternative embodiment of the method of the present invention showing a bilateral approach to the vertebra. Such a bilateral approach would preferably be done in order of first one side and then the other, although the figure depicts both steps simultaneously.

As depicted in FIG. 17, in an alternative embodiment of the process of the present invention the surgery can be done as a bilateral procedure by first infusing the failed vertebra from one side and then repeating the entire process from the opposite side of the vertebra. By such a bilateral approach, it is possible for the physician, if he desires, to substantially fill all of the porous structure of the cancellous bone of the vertebra.

Figure 18:
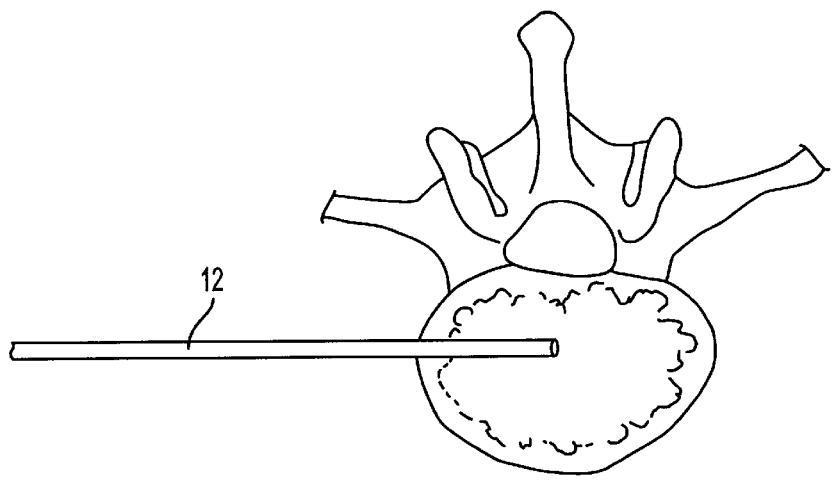
FIG. 18 is a depiction of a second alternative embodiment of the method of the present invention in which the cancellous bone is penetrated with minimal disruption of the cancellous bone to permit more extensive infusion of the injectable material.

As depicted in FIG. 18, a further alternative embodiment of the process of the present invention could include the step of extending the guide wire 2 further into the cancellous bone of the vertebra and thus positioning the material conduit 14 of the delivery cannulae 12 more central to the cancellous bone portion of the vertebrae. As the porous structure of the cancellous bone is infused with bone cement using this alternative process, the delivery cannulae 12 can be slowly withdrawn from the cancellous bone structure while continuing to infuse the bone with bone cement. The result would be a substantially filled vertebrae using a unilateral process.

Figure 19:
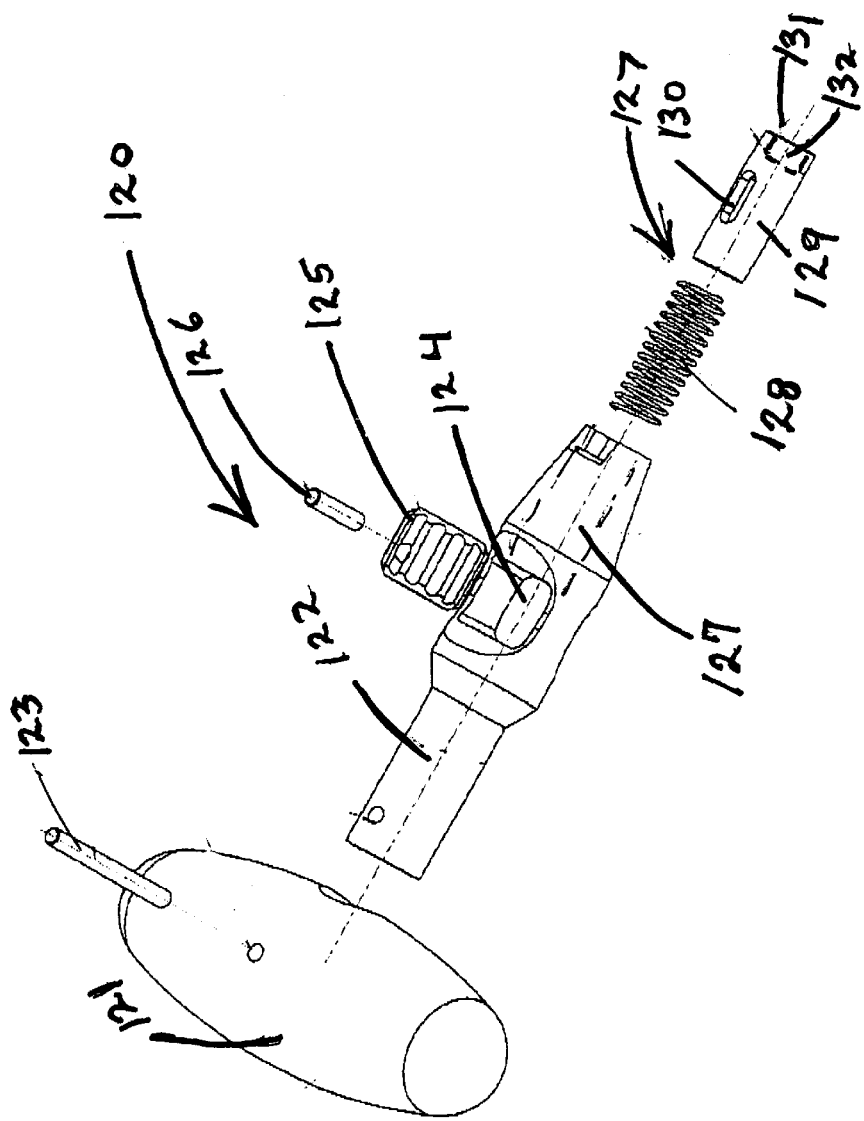
FIG. 19 is a depiction of an exploded view of an adjustable handle member for use with the present invention.

As depicted in FIG. 19, an adjustable handle member, generally shown as 120 in an exploded view, can be employed with the present invention. While the preferred embodiment of this adjustable handle member 120 can have a T shaped grip 121 to improve the users grip for turning the device, it is within the concept of the invention to have a handle of any shape, which is suited for manual use. The handle shaft 122, can be removably connected to the grip 121 by a grip connector 123. Located within a recess 124 of the handle shaft is an adjustment control 125, which preferably can be in the form of a thumb wheel although other equivalent embodiments are within the concept of the invention. The adjustment control can have an adjustment connector 126, which can be in the configuration of a pin. Within the handle shaft 122, a lumen 127 is provided which can contain a torque connector assembly, generally shown at 127. The torque connector assembly 127 includes a tensioner 128, which is surrounded by a hollow torque sleeve 129. The torque sleeve 129 is provided with an adjustment connector receiving slot 130, which cooperates in a pin-slot manner with the adjustment connector 126. The torque sleeve 129 at its most distal end 131 is provided with a sleeve connection member 132, the sleeve connection member 132 preferably being a female luerlock, although other type connectors can also be used. In operation, as the adjustment control 125 is manually operated, it causes a corresponding movement in the adjustment connector 126. The adjustment connector 126 being in a pin-slot, or equivalent, operating arrangement with the torque sleeve 129 causes a movement of the torque sleeve so as to effect an engagement of the sleeve connection member 132 at the distal end 131 of the torque connector 129 to a complementary connector, preferably a male luerlock, on a cannulae or guide wire of the present invention. The tensioner 128, which is retained within the torque connector 129 serves to maintain tension on the assembly during operation.

Figure 20:
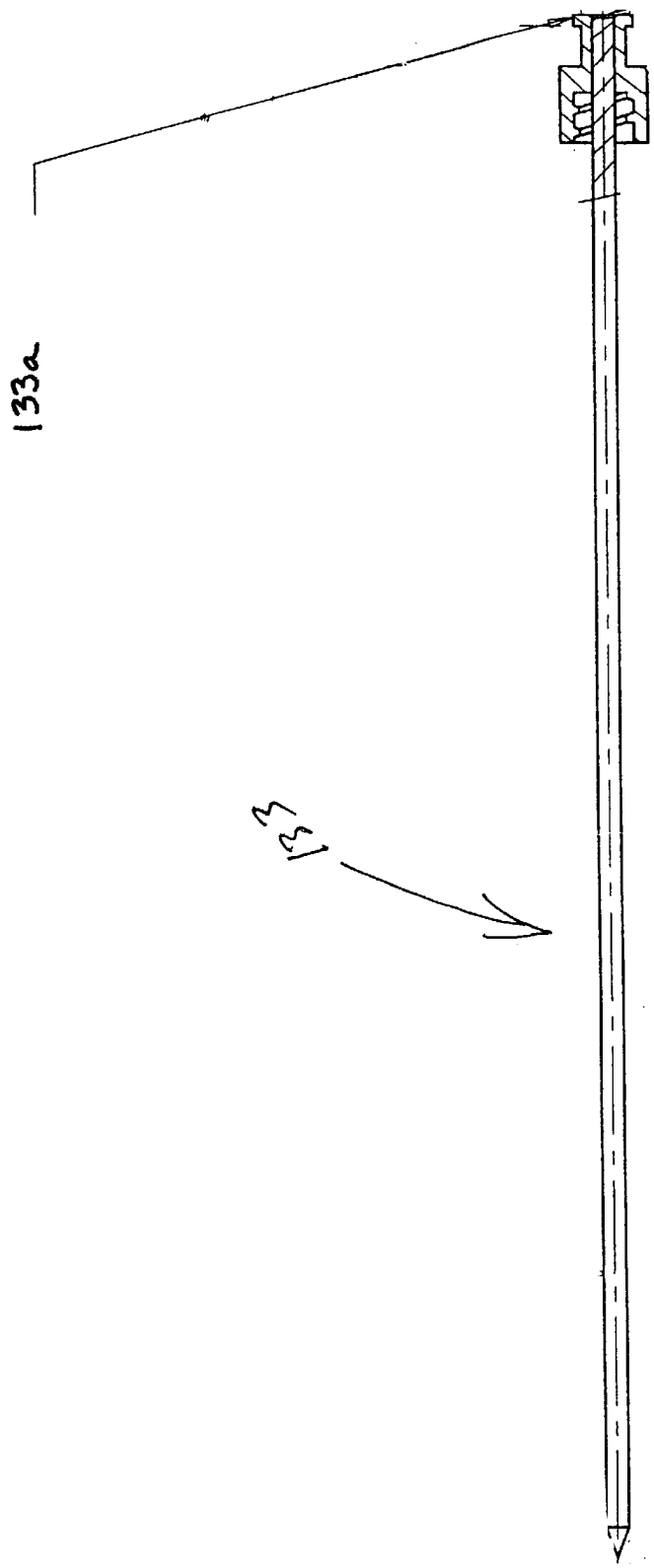
FIG. 20 is a small stature luerlock guide wire for use with the present invention.

As depicted in FIG. 20 a small stature luerlock guide wire 133 can be provide for use in particularly small areas of operation. While used primarily for small areas of operation, the small stature luerlock guide wire 133 can be made in any size as needed. Further, the guide wire 133 is provided with a luerlock connector 133*a* for ease of connection to any handle complementarily equipped. Other configurations of connectors can also be employed within the concept of the invention.

Figure 21:
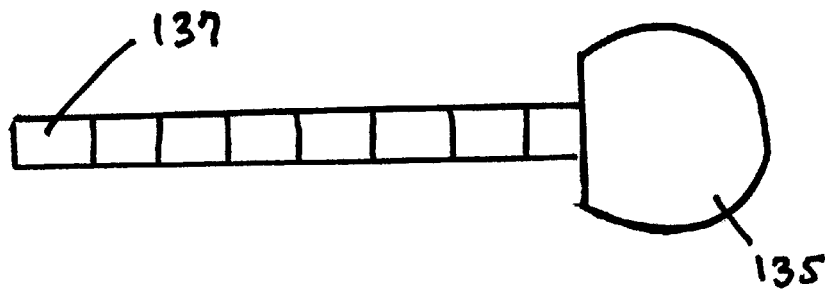
FIGS. 21A, 21B and 21C are depictions of a loading syringe assembly for use with the present invention.
Figure 21:
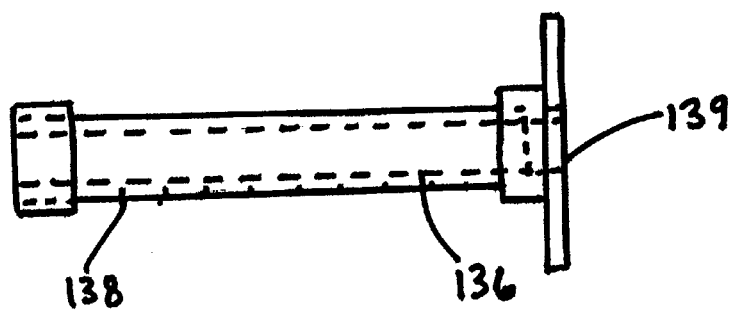
Figure 21:
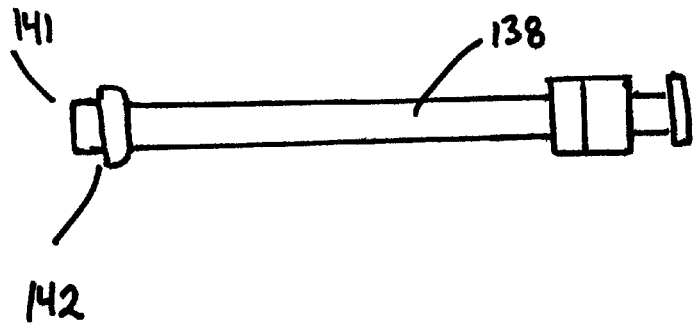

As depicted in FIGS. 21A, 21B and 21C, a loading syringe, generally shown at 134 is provided with a loading syringe plunger and handle assembly 135 and a loading syringe vessel 136. The loading syringe plunger and the loading syringe vessel 136 can be provided with graduated indicia 137, 138 to assist the user in determining the volume of material loaded in the syringe as well as the volume expelled during operation. The loading syringe 134 can also be provided with a flexible loading syringe connector tube 138, which provides flexible connection between the parts of the assembly. Connection between parts of the assembly are preferably by luerlock, although other connectors are within the scope of the invention. The proximal end 139 of the syringe vessel 136 can be provided with a threaded connector 140, which cooperates with a complimentary threaded connector 141 on the proximal end 142 of the flexible loading syringe connector tube 138. This entire assembly can be used as a means to facilitate loading of material into the cannulae of the present invention.

As depicted in FIG. 22, hand operated syringe gun, generally shown at 142 is provided, which can be used to facilitate the accurate expulsion of material from the cannulae of the present invention. The syringe gun 142 is preferably hand operated, however, it is within the concept of the invention to provide a mechanical or computer controlled assist to operate the syringe gun 142. In its preferred configuration of manual operation, the syringe gun 142 is provided with a gun gripping member 143 and an operably connected gun actuator 144. Upon operation of the actuator 144, the driving member 145, which is preferably formed in a rod-like configuration, is moved in carefully graduated amounts so as to force the integrally assembled plunger member 146 into a removably connected gun syringe tube 147. Flow control members can be disposed along the length of the driving member 145. The flow control members can operationally interact with the actuator 144 to limit flow of material out of the syringe gun 142 to as little as 1 cc of material per actuation by an operator. The syringe tube 147 can be removably mounted onto the syringe gun by a standard luerlock type connection or any other connection known in the art. In operation, as the plunger member 146 moves through the lumen of the syringe tube 147, the air contained within the lumen is vented through air vents 148, which can be formed in at least one of the concentrically arranged plunger ribs 149 which form a sliding connection between the interior wall of the syringe tube 147 and the plunger member 146. The air vents 148 are preferably multiple and not aligned with air vents 148 for sequentially placed plunger ribs 149. This arrangement permits air within the syringe tube 147 to escape during operation without the loss of the fluid contents of the syringe tube.

It should be known that while the surgical process of the present invention described above is particularly appropriate to provide fixation of vertebral compression failures due to osteoporosis, tumor or other pathogenic bone conditions, the process can also be used in cases of trauma induced compression failures. Further, it is possible that the process could be used as a preventive or protective measure that could conceivably be used for patients, which present themselves as being extremely likely to suffer vertebral compression failures.

What we claim is:

1. An injection device comprising:
   a delivery cannulae having a proximal end and a distal end, which are connected by a cannulae body, with a proximal end and a distal end, said cannulae body having indicia disposed along at least a portion of said cannulae body between said distal end and said proximal end and having a lumen capable of acting as a material conduit,
   said lumen passing from said proximal end through said distal end;
   an elongated plunger, said plunger being sized and configured to slidably pass through said lumen;
   a removable handle configured for secure attachment to said proximal end of said delivery cannulae, said delivery cannulae being equipped with a handle retention member integrally formed in said proximal end of said delivery cannulae.

2. An injection device according to claim 1, wherein said indicia are graduated indicia, said indicia being radioopaque and said delivery cannulae being radiotranslucent.

3. An injection device according to claim 1, wherein said delivery cannulae is radioopaque and said indicia are graduated indicia and are radiotranslucent.

4. An injection device according to claim 1, further comprising:
   an elongated guide wire, said guide wire having a first end and a second end connected by a elongated guide wire body, and said first end being configured with a taper, said taper being capable of breaching cortical bone sufficient to form a channel through said cortical bone, wherein said delivery cannulae is sized and configured to slidably pass circumferentially over said guide wire.

5. An injection device according to claim 4, wherein said injectable material is selected from the group consisting of bone cement, antibiotics, cellular implants, natural products of cells recombinant nucleic acid products, protein products of recombinant cells.

6. A kit for introducing an injectable material into a subject, the kit comprising:
an injection device according to claim 1; and
an injectable material selected from the group consisting of bone cement, antibiotics, whole cellular implants, natural products of cells, recombinant nucleic products and protein products of recombinant cells.

7. A kit according to claim 6, wherein said injectable material is polymethylmethacrylate.

8. An injection device according to claim 1, further comprising:
an elongated guide wire, said guide wire having a first end and a second end connected by an elongated guide wire body, said first end being configured with a taper, said taper being capable of breaching cortical bone sufficient to form a channel through said cortical bone; and
an aligning cannulae having a gripping end and a tapered end, said aligning cannulae being sized and configured to slidably pass circumferentially over said guide wire and said delivery cannulae being sized and configured to slidably pass circumferentially over said aligning cannulae.

9. An injection device according to claim 8, wherein said plunger comprises a mixing tip.

10. An injection device according to claim 8, wherein said device is formed of materials selected from the group consisting of stainless steel, anodized aluminum, thermoplastics and glass.

11. An injection device according to claim 8, wherein said delivery cannulae lumen comprises multiple lumens.

12. An injection device according to claim 8, wherein said guide wire further comprises a removable handle.

13. An injection device according to claim 12, wherein said removable handle comprises removable proximal end.

14. An injection device according to claim 8, wherein said second end of said guide wire comprises an attached longitudinally aligned Luer lock connector.

15. An injection device according to claim 14, wherein said handle comprises a Luer lock configured to releasably engage said Luer lock connector of said guide wire, said handle further comprising a longitudinally aligned lumen opening at each end of said handle.

16. An injection device according to claim 8, wherein said guide wire comprises graduated guide wire indicia disposed along said guide wire body between said first end and said second end of said guide wire body.

17. An injection device according to claim 16, wherein said guide wire comprises indicia disposed along at least a portion of the length of said guide wire.

18. An injection device according to claim 17, wherein said guide wire indicia are radiotranslucent and said guide wire is radioopaque.

19. An injection device comprising:
a delivery cannulae having a proximal end and a distal end, which are connected by a cannulae body, with a proximal end and a distal end, said cannulae body having said lumen having graduate indicia disposed along at least a portion of said cannulae body between said distal end and said proximal end and a lumen capable of acting as a material conduit, said lumen passing from said proximal end through said distal end;
a syringe system releasably connected to said delivery cannulae and in fluid communication with said cannulae lumen;
a removable handle configured for secure attachment to said proximal end of said delivery cannulae, said delivery cannulae being equipped with a handle retention member integrally formed in said proximal end of said delivery cannulae.

20. An injection device according to claim 19, wherein said syringe system is connected to said delivery cannulae by a flexible conduit.

21. A kit for introducing an injectable material into a subject, the kit comprising:
an injection device according to claim 19; and
an injectable material selected from the group consisting of bone cement, antibiotics, whole cellular implants, natural products of cells, recombinant nucleic products and protein products of recombinant cells.

22. An injection device according to claim 19, wherein said syringe system comprises an automated impelling unit.

23. An injection device according to claim 22, wherein said automated impelling unit being capable of controlling the rate and amount of movement of the mechanism of said syringe system.

24. An injection device according to claim 23, wherein said automated impelling unit further comprises a pressure sensing unit.

25. An injection device according to claim 19, wherein said syringe system is removably connected to said delivery cannulae by a connector selected from the group consisting of a Luer lock, a bayonet fitting, and a hydraulic quick disconnect fitting.

26. An injection device according to claim 25, wherein said connector is integral with said proximal end of said delivery cannulae and is aligned with the longitudinal axis of said delivery cannulae body.

27. An injection device according to claim 25, wherein said connector of said delivery cannulae is a Luer lock and said handle comprises a Luer lock configured to releasably engage said Luer lock connector of said delivery cannulae, said handle further comprising a longitudinally aligned handle lumen opening at each end of said handle, said handle lumen being in fluid communication with said lumen of said delivery cannulae.

28. An injection device according to claim 27, wherein said handle further comprises a removable proximal Luer lock end.

29. An injection device according to claim 27, wherein said handle further comprise a view slot sized and configured to permit viewing of the handle lumen.

30. An injection device according to claim 27, wherein said handle further comprises a first clearance hole passing through said handle perpendicular to said handle lumen, said first clearance hole being sized and configured to slidably receive said guide wire.

31. An injection device according to claim 30, wherein said handle further comprises a second clearance hole passing through said handle perpendicular to said handle lumen, said second clearance hole being sized and configured to slidably receive said aligning cannulae.

32. A surgical device for finding the pedicle portion of a vertebra of a subject comprising:
a guide wire, said guide wire having a connection member;
a guide wire handle configured for connection to said guide wire connection member; and
a cannulae sized and configured to pass over said guide wire.

* * * * *